(12) United States Patent
Everett

(10) Patent No.: US 12,207,877 B2
(45) Date of Patent: Jan. 28, 2025

(54) SLIT-SCANNING FUNDUS IMAGER ENHANCEMENTS

(71) Applicants: Carl Zeiss Meditec AG, Jena (DE); Carl Zeiss Meditec, Inc., Dublin, CA (US)

(72) Inventor: Matthew J. Everett, Livermore, CA (US)

(73) Assignees: Carl Zeiss Meditec, Inc., Dublin, CA (US); Carl Zeiss Meditec AG, Jena (DE)

( * ) Notice: Subject to any disclaimer, the term of this patent is extended or adjusted under 35 U.S.C. 154(b) by 768 days.

(21) Appl. No.: 17/275,595

(22) PCT Filed: Sep. 24, 2019

(86) PCT No.: PCT/EP2019/075769
§ 371 (c)(1),
(2) Date: Mar. 11, 2021

(87) PCT Pub. No.: WO2020/064777
PCT Pub. Date: Apr. 2, 2020

(65) Prior Publication Data
US 2022/0095913 A1    Mar. 31, 2022

Related U.S. Application Data

(60) Provisional application No. 62/736,213, filed on Sep. 25, 2018.

(51) Int. Cl.
*A61B 3/12* (2006.01)
*A61B 3/10* (2006.01)
*A61B 3/15* (2006.01)

(52) U.S. Cl.
CPC .......... *A61B 3/1225* (2013.01); *A61B 3/1025* (2013.01); *A61B 3/156* (2013.01)

(58) Field of Classification Search
CPC ............ C03C 10/0009; C03C 10/0018; C03C 10/0027; C03C 10/0054; C03C 3/091;
(Continued)

(56) References Cited

U.S. PATENT DOCUMENTS 3,915,564 A   10/1975   Urban
4,452,517 A    6/1984   Kohayakawa
(Continued)

FOREIGN PATENT DOCUMENTS

CN   108272432       7/2018
EP      223356 A2    5/1987
(Continued)

OTHER PUBLICATIONS

JPO, Japanese Office Action dated Aug. 1, 2023 in Application No. 2021-516450.
(Continued)

*Primary Examiner* — Brandi N Thomas
(74) *Attorney, Agent, or Firm* — Snell & Wilmer L.L.P.

(57) ABSTRACT

A scan imaging system has a scanning component that receives light from a light source, and creates a scanning beam that is directed by an optic train to a sample to be imaged. A camera captures light returning from the sample to construct an image. Reflexes on a target lens within the optic train are prevented by one or more light blocks. A first light block, imaged to the target lens, is positioned in a light path from the light source to the scanning component to create a first moving dark zone on the target lens through which the scanning beam from the scanning component to the sample may not pass. A second light block, also imaged to the target lens, is positioned in a light path from the sample to the collector to create a second moving dark zone on the target lens through which light returning from the sample
(Continued)

may not pass. The moving dark zones maintain the scanning beam separate from the returning light on the target lens.

25 Claims, 8 Drawing Sheets

(58) Field of Classification Search
CPC ......... C03C 3/097; C03C 3/118; C03C 4/082; C03C 4/085; C03C 21/001; C03C 2204/00; C03C 3/093; C03C 4/02; C03C 10/00; C03C 21/002; C03C 3/062; C03C 3/087; C03C 3/089; G02B 21/002; G02B 1/02; G02B 21/0032; G02B 21/0048; G02B 21/367; G02B 27/58; G02B 21/0076; G02B 21/10; G02B 21/0024; G02B 21/0072; G02B 21/0056; G02B 21/006; G02B 21/0064; G02B 21/008; G02B 21/0084; G02B 21/0028; G02B 21/16; G02B 27/46; A61B 3/1025; A61B 3/1225; A61B 3/156; A61B 3/102; A61B 3/107; A61B 6/06; A61B 6/4092; A61B 6/4233; A61B 6/4291; A61B 6/484; A61B 6/502; A61B 6/5252; A61B 5/0075; A61B 5/445; A61B 5/4842; A61B 5/7267; A61B 5/7275

See application file for complete search history.

(56) References Cited

U.S. PATENT DOCUMENTS

| | | | |
|---|---|---|---|
| 4,991,953 | A | 2/1991 | Pflibsen et al. |
| 5,168,157 | A | 12/1992 | Kimura |
| 5,784,148 | A | 7/1998 | Heacock |
| 8,488,895 | B2 | 7/2013 | Muller et al. |
| 8,783,868 | B2 | 7/2014 | Qiu et al. |
| 9,549,672 | B2 | 1/2017 | Westphal et al. |
| 2005/0134797 | A1 | 6/2005 | Grove |
| 2006/0092376 | A1 | 5/2006 | Baek et al. |
| 2006/0114411 | A1 | 6/2006 | Wei et al. |
| 2007/0291277 | A1 | 12/2007 | Everett et al. |
| 2009/0244482 | A1* | 10/2009 | Elsner .................. A61B 3/1025 351/206 |
| 2011/0267583 | A1 | 11/2011 | Hayashi |
| 2015/0131050 | A1 | 5/2015 | Bublitz et al. |
| 2017/0049323 | A1 | 2/2017 | Bublitz |
| 2018/0014727 | A1 | 1/2018 | Bublitz et al. |

FOREIGN PATENT DOCUMENTS

| | | |
|---|---|---|
| JP | H07178054 | 7/1995 |
| JP | 2009538697 | 11/2009 |
| JP | 2018-000620 | 1/2018 |
| JP | 2018504219 | 2/2018 |

OTHER PUBLICATIONS

India Patent Office, Exam Report dated Jan. 1, 2023 in IN Serial No. 202117018388.
International Search Report and Written Opinion for International Patent Application No. PCT/EP2019/075769, mailed on Jan. 8, 2020, 13 pages.
CNIPA, First Office Action dated Mar. 28, 2024 in CN Serial No. 201980062815.3.
CNIPA, Second Office Action dated Sep. 29, 2024 in CN Serial No. 201980062815.3.

* cited by examiner

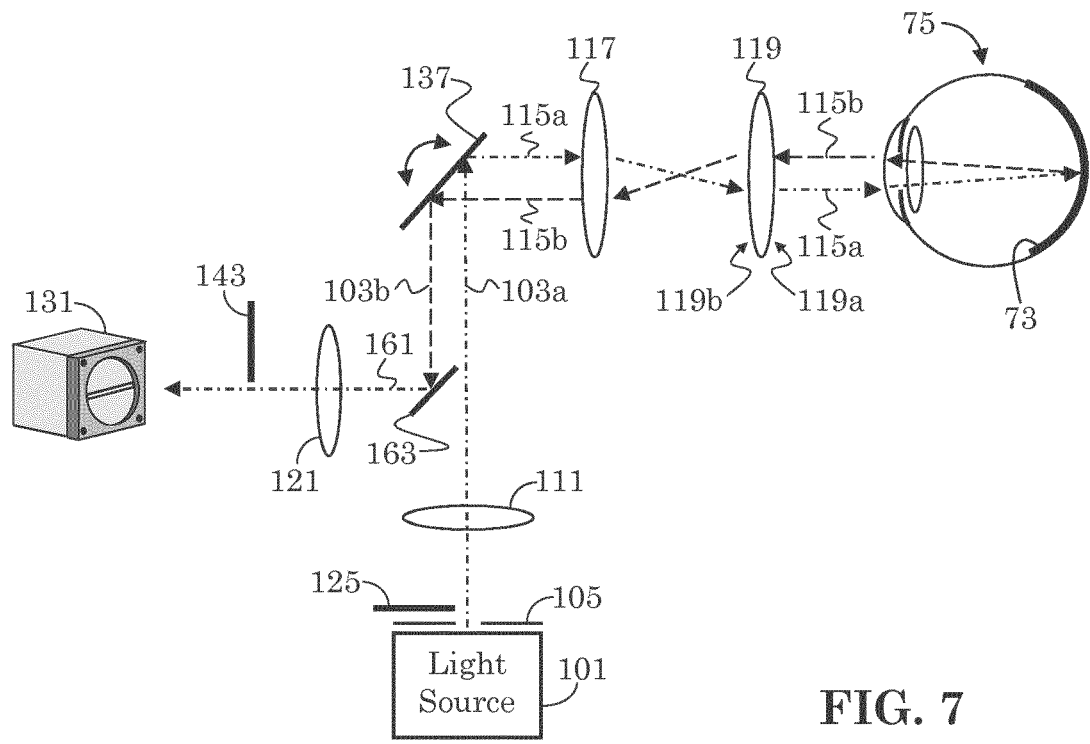
FIG. 7
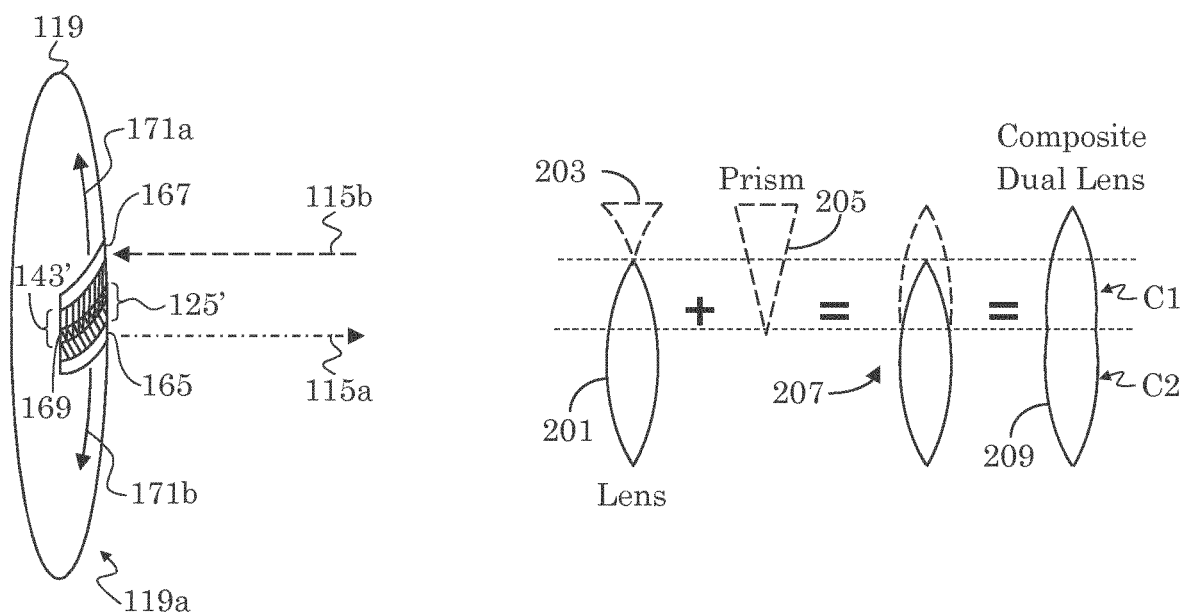
FIG. 8
FIG. 10

SLIT-SCANNING FUNDUS IMAGER ENHANCEMENTS

PRIORITY

This application is a National Phase application under 35 U.S.C. § 371 of International Application No. PCT/EP2019/075769, filed Sep. 24, 2019, which claims priority to U.S. Provisional Application Ser. No. 62/736,213, filed Sep. 25, 2018, the contents of which are hereby incorporated by reference in their entirety.

FIELD OF INVENTION

The present invention is generally directed to the field of scan imagers. More specifically, it is directed to reducing image artifacts caused by reflexes from internal optics of a scan imager, and in particular, a fundus scan imager.

BACKGROUND

Various different types of image-capture devices for imaging a sample under test are known. Of particular interest are imaging systems capable of taking close-up images of a specimen with sufficient detail, e.g., sufficient focus, lighting, magnification, and signal-to-noise ratio (SNR). An example of such an imaging system is a fundus imager, which is typically used to image the fundus of an eye. The fundus is the interior surface of the eye opposite the eye lens and may include the retina, optic disc, macula, fovea, and posterior pole. Two categories of imaging systems used to image the fundus are flood illumination imaging systems (or flood illumination imagers) and scan illumination imaging systems (or scan imagers).

Flood illumination imagers flood with light an entire field-of-view (FOV) of interest of a specimen at the same time, such as by use of a flash lamp, and take an image of the specimen (e.g., the fundus) with a full-frame camera. FIG. 1 is a conceptual illustration of a flood illumination fundus imager 10. A flash-tube 15 is shown as an illumination source, whose illumination light follows an optical path along illumination axis 17, which may include various system lenses 19, and is folded by mirror 23 onto optical axis 25, which includes system lens 11, to be conveyed to the sample, or a specimen, to be imaged (e.g., the retina 33 of eye 13 in the present example). System lens 11 is the imager lens closest to the eye 13, and may herein be termed an ocular lens or ophthalmic lens. Optical axis 25 traverses the optical components of the eye 13 (including the cornea 27, iris 28, pupil 29, and crystalline lens (or eye lens) 31) to reach the retina 33. Thus, illumination light traveling along optical axis 25 may enter the eye 13 through its cornea 27, pass through its pupil 29, and traverse crystalline lens 31 to reach the retina 33 at the back of the eye (e.g., the fundus area), and be scattered by the retina 33 (and other parts of the fundus). Scattered light returning from the fundus 33 may exit through the crystalline lens 31, pupil 29, and cornea 27, and travel along optical axis 25 to a viewing axis 35. Viewing axis 35 may include multiple system lenses 21, and directs the scattered light returning from the fundus to a full-frame camera 37, which captures a full-frame image 39 of the fundus of eye 13. Since viewing axis 35 and illumination axis 17 are coincident along optical axis 25, mirror 23 typically has a centrally located aperture 43 used to permit scattered light returning from eye 13 to pass through mirror 23 onto viewing axis 35 to be captured by camera 37. Mirror 23 may be flat and annular (e.g., ring-shaped) with a round aperture 43 at its center. Mirror 23 may further be imaged to the pupil 29 if it is used for pupil splitting.

Pupil splitting permits illumination light (light entering the eye 13) and returning light (scattered light exiting the eye) to following different paths into and out of the eye 13 at optimally chosen regions of the pupil 29. These regions may be chosen, for example, to avoid pupil clipping, light scattering from cataracts, and specular reflections (e.g., reflexes) of illumination light, such as from the cornea 27. To ease implementation of pupil splitting, mirror 23, which reflects illumination light towards the eye 13 and whose aperture 43 permits passage of returning light to the camera 37, may be imaged to, or near, the pupil 29. For example, when mirror 23 folds (e.g., reflects) illumination light from illumination axis 17 onto optical axis 25 towards eye 13, an annular-shape illumination region may be created at the eye 13. That is, round aperture 43 of mirror 23 may create a round, non-illuminated region near the cornea 27 at the center of the annular-shape illumination region. Scattered light returning from the retina 33 may exit the eye 13 through this non-illuminated region and thereby avoid illumination light entering the eye 13. Additionally, specular artifacts from optical surfaces of the flood illumination imager itself may be reduced by using so-called dark spots, which are stationary in illumination paths, to prevent certain surface areas of system optics from being illuminated. Flood illumination imaging systems may image a fundus quickly, and have a high signal level and dynamic range, but may suffer from issues of low contrast. The need to eliminate reflexes may also place constraints on the system which may limit its FOV. An example of a flood illumination imaging system is found in U.S. Pat. No. 3,915,564, assigned to the same assignee as the present invention, and herein incorporated in its entirety by reference.

By contrast, scan imagers illuminate and image only a portion of a sample at a time, and collect multiple image portions as an illumination beam is scanned across the sample. The multiple image portions may then be stitched together, or montaged, to create a composite image, which may constitute a full-frame image. A benefit of scan imagers over the flood illumination imagers is an increased level of confocality, which provides greater discrimination against undesirable light scattered from surfaces other than the retina, enabling wider FOV, artifact-free imaging. Like flood illumination imagers, fundus scan imagers suffer from reflex issues at various optical components of the eye and at various system lenses of the scan imager itself, although to a lesser degree. Techniques for reducing reflexes at optical components of the eye, such as pupil splitting, may be applied to scan imagers. Pupil splitting may provide some level of reflex reduction, but does not eliminate it, and its benefits are targeted at minimizing unwanted light from the eye, rather than from a specific system lens.

It is an object of the present invention to provide a scan imager with a mechanism to directly reduce or blocks reflexes from specific system lenses.

It is a further object of the present invention to provide a fundus scan imager with reduced reflexes at a given target optic/lens of the fundus scan imager.

SUMMARY OF INVENTION

The above objects are met in a system, device, and/or method for directly reducing or eliminating reflex (e.g., reflection) artifacts at a given target optic (e.g., a system optic such as a lens, prism, mirror, etc.) within a scan imager (or scan illumination imaging system), and particularly in a scan imager configured as a fundus scan imager. The scan imager may include a radiation source (e.g., light source) and a scanning component. The radiation source may be a coherent light source, such as a laser, or a non-coherent light source, such a lamp or light emitting diodes (LEDs). The scanning component may be one or more mirror galvanometer, micro electro mechanical system (MEMS) scanner, electro-optical deflector, rotating mirror, and/or rotating polygon scanner, or other scanning mechanism. The scanning component receives a radiation stream (e.g., laser beam or light beam) from the radiation source, and defines a scan beam (e.g., by rotation of a deflecting mirror within the galvanometer). The scan beam may be scanned across the sample to be imaged, and thereby create a moving region of illumination on the sample. In the case of a fundus scan imager, the sample would be the fundus (or retina) of the eye, and the scanning component may be imaged to the pupil of an eye to facilitate pupil splitting, as explained above.

System optics (e.g., a scan lens and an ocular, or ophthalmic, lens) may direct the scan beam from the scanning component to the sample to be imaged. The system optics may constitute an optic train that defines a radiation path (e.g., light path) from the scanning component to the sample being imaged. Optionally, the target optic on which reflexes are to be eliminated may be selected from within this optic train. The scan beam may be scanned across the target optic. A radiation-blocking component (e.g., a first light block) may be positioned to partially block the radiation stream output from the radiation source and to limit the radiation received by the scanning component. Thus, the radiation-blocking component may be positioned along a radiation path from the radiation source to the scanning component. The radiation-blocking component may be imaged to (e.g., positioned at a conjugate plane of) the target optic and create a moving non-radiation zone (e.g., a first dark zone) on the target optic through which the scan beam from the scanning component cannot pass. The scan beam may define a moving illumination region, and the non-radiation zone may move in conjunction with the illumination region. Optionally, the non-radiation zone may block (or partially block) an overlap between the illumination region and a collection region (through which scattered light returning from the sample may pass), particularly at the target optic.

The scan imager may include a collector (e.g., a photodetector, photo-sensor, charge coupled device (CCD) image sensor, or complementary metal-oxide-semiconductor (CMOS) image sensor) for collecting scattered radiation (e.g., scattered light) returning from the sample through the collection region. The scan imager may further include a collector-blocking component (e.g., a second light block) positioned to partially block the collection region so as to block the amount of returning, scattered radiation that reaches the collector. The collector-blocking component may be imaged to (e.g., located at a conjugate plane of) the target optic (or a second target optic) and thereby create a moving non-collection zone (e.g. a second dark zone) on the target optic (or the second target optic) through which scattered radiation returning from the moving region of illumination cannot pass. The non-collection zone may be made to move by the scanning component, and may overlap the collection region. For example, the non-collection zone may move in conjunction with the non-radiation zone and the scan beam, and may block (or partially block) an overlap between the illumination region and the collection region, particularly at the target optic(s). Blocking of the overlap between the illumination region and the collection region may be achieved by having the non-collection zone and non-radiation zone abut or overlap each other, for example, as they move (e.g., in conjunction/unison with each other) on the target optic(s).

The blocking of the overlap between the illumination region and collection region on the target lens limits (or blocks) reflections from the target lens from reaching the collector, and thereby helps to avoid reflex artifacts in a captured image. Thus, minimizing, or eliminating, the overlap between the illumination and collection regions on the target lens for any given scan position of the scanning component may be desirable. However, system focus adjustments, which may be a part of a typical setup routine for an image capture sequence, may defocus and/or shift the position of the non-radiation zone and/or non-collection zone, leading to increased overlap between the illumination and collection regions. Various steps for compensating for this defocusing effect are contemplated.

Although it is desirable to completely block the overlap between illumination and collection regions, adjustments in system focus may alter (e.g., enlarge) the size of the overlap between the illumination and collection regions. The size and positioning of the collector-blocking component and radiation-blocking component may be selected so that the overlap between the moving non-radiation zone and non-collection zone on the target optic is sufficient to cover a predefined increase in overlap between illumination and collection regions, such as due to defocusing effects resulting from the position of the conjugate plane of the target lens being axially moved relative to the collector-blocking component and/or radiation-blocking component.

In the case of the scan imager being a fundus scan imager imaging a highly myopic eye, the conjugate plane of the target lens may be moved (e.g., axially) relative to the blocking component(s) as a result of compensating for the eye's myopia. In some instances of severe myopia, due to blocker position(s) moving relative to illumination region and/or collection region, the non-collection zone and/or non-illumination zone may limit too much light (to or from the eye) leading to darkened images or to slow image capture cycles. In these extreme cases, it may be desirable to accept some degree of reflex in return for brighter images. That is, the collector-blocking component and/or radiation-blocking component may be configured to be movable (or removable) so as to limit its obstruction of a radiation path (e.g., optical path). For example, the radiation-blocking component may be positioned to partially block radiation output from the radiation source and the collector-blocking component may be positioned to partially block scattered radiation returning from the moving collection region, or the radiation-blocking component may be positioned to not obstruct radiation output from the radiation source and/or the collector-blocking component may be positioned to not obstruct scattered radiation returning from the moving collection region.

Alternatively, if the scan imager has a focus-adjustment mechanism that causes the conjugate plane of the target optic to move (e.g., axially) as the sample is brought into focus on the collector, the collector-blocking component and/or the radiation-blocking component may be moved in conjunction with the conjugate plane of the target optic to remain substantially at the conjugate plane of the target optic. This may be caused, for example, by movement of optics between a blocker and the target lens (including the target lens) as focus is adjusted for eye myopia. In other words, the blocking component(s) may be moved as focus is adjusted to keep it at the conjugate plane of the target lens.

Optionally, the position of the radiation-blocking component may remain static irrespective of movement of the conjugate plane of the target optic.

Further alternatively, the relative positions of the collector-blocking component, scanning component, and target optic may be independent of a focusing mechanism. For example, the focus-adjusting optics may be positioned between the collector-blocking component and the collector so that the relative positions the optics along an optical path of the returning scattered radiation from the target optic element to the collector-blocking component (including the scanning component) remained fixed even as the focus-adjusting optics bring the sample into focus on the collector.

Additionally, a change in blocking component position relative to an illumination and/or collection plane may affect the amount of light that is captured. This change in position may be due to movement in an optical chain (e.g., between the radiation source and the radiation-blocking component and/or between the collector and the collector-blocking component), or may be due to movement of blocking component to keep it at the conjugate plane of the target lens, as described above. This change in position may result in increased blocking of light as the camera focus is adjusted for greater myopia. Therefore, one might adjust the amount of blocking provided by either blocking component to let more light through for more myopic cases, even if this results in some increase in reflexes returning to the collector.

In a particular embodiment, the radiation-blocking component may be made coplanar with the collector-blocking component. This may simplify design and alignment of the scan imager. Additionally, an illumination aperture at the conjugate plane of a surface of the sample to be imaged (e.g., an eye retina in the case of a fundus imagers) may be placed in front of the radiation source to configure (e.g., shape) its output radiation beam. In this case, the illumination aperture may be between the illumination source and the radiation-blocking component. Similarly, the scan imager may have a collection aperture at the conjugate plane of the surface (optionally, the same surface) of the sample to be imaged (e.g., eye retina). In this case, the collection aperture may be positioned between the collector and the collector-blocking component, and the illumination aperture may be made coplanar with the collection aperture. The illumination aperture may match the collection aperture, and be at the conjugate plane of the collection aperture on the light sensor (e.g. collector).

Optionally, the scan imager may further include a pupil-splitting aperture that defines a splitting region that separates the scan beam of radiation in front of the sample (e.g., retina or fundus) from scattered radiation returning from the sample. For example, in the case of pupil splitting in a fundus imager, the pupil-splitting aperture may be substantially positioned immediately preceding the scanning component in a radiation path from the radiation source to the scanning component. This splitting region may define a first sample-opening through which the radiation beam from the radiation source passes to reach the scanning component, and define a second sample-opening through which scattered radiation returning from the sample passes. The first sample-opening and second sample-opening may be coplanar. In this configuration, the scan imager may further include a dual lens embodied by two coplanar lenses molded as a single optic component, and including a first sub-lens aligned with the first sample-opening and a second sub-lens aligned to the second sample-opening. A structure (e.g. a wall) may maintain alignment between the first sample-opening, the first sub-lens, the radiation-blocking component, and the illumination aperture, and maintain alignment between the second sample-opening, the second sub-lens, the collector-blocking component, and the collector aperture. This structure may also serve to prevent light leakage from the first sample-aperture side to the second sample-aperture side.

In the case of the scan imager being a fundus imager, the target lens may be a transmissive lens. For example, the target lens may be the lens closest to the sample (e.g. eye fundus) on the radiation path from the scanning component to the sample. Alternatively, the target optic may be, for example, a scan lens between the scanning component and the sample and whose function is generally to receive the scan beam from the scanning component at an incident angle and to output the scan beam along a predefined, generally collimated path.

The scan imager may be a confocal point scanning imager or a line scanning imager. As it would be understood, a line scanning imager (or line scanning ophthalmoscope) may include both a line-scanning laser scanner/ophthalmoscope (LSLO) or broad-line scanning (fundus) imager/ophthalmoscope (BLFI). In the case of the scan imager being a line scanning imager, the radiation beam may be a substantially rectangular beam of radiation. The rectangular beam of radiation may have a (optionally fixed) length dimension and may have a variable width dimension substantially perpendicular to the length dimension.

The present scan imager may be implemented in different types of scan configurations. For example, the scan imager may be a scan-non-descan system, a scan-descan system, or a scan-descan-rescan system.

Other objects and attainments together with a fuller understanding of the invention will become apparent and appreciated by referring to the following description and claims taken in conjunction with the accompanying drawings.

The embodiments disclosed herein are only examples, and the scope of this disclosure is not limited to them. Any embodiment feature mentioned in one claim category, e.g. method, can be claimed in another claim category, e.g. system, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts:

FIG. 7 illustrate an alternate scan-descan configuration example of a line scanning fundus imager incorporating the present invention.

FIG. 8 provides a simplified, not to scale, and close-up view of the ophthalmic lens of FIG. 7, along with the imaged illumination block (e.g., a non-illumination zone), imaged collection block (e.g., non-collection zone), an illumination window through which a scan beam from the scanning component may pass to reach the eye, and a collection window through which returning light from the eye may pass to reach the collector.

FIG. 10 illustrates a conceptual design of a composite dual lens.

DESCRIPTION OF THE PREFERRED EMBODIMENTS

Figure 1:
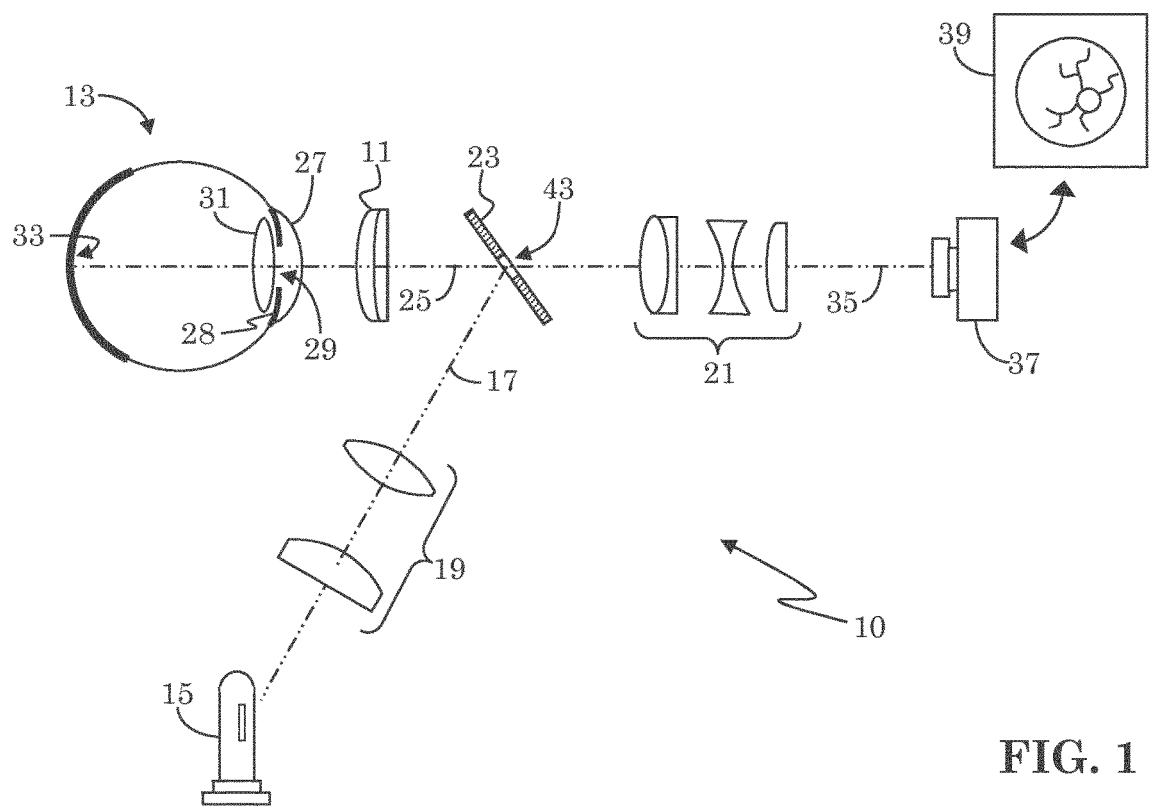
FIG. 1 is a conceptual illustration of a flood illumination fundus imager.

Two types of scan imagers are the confocal point scanning imager (which uses a laser point beam to scan a sample one point at a time) and the line scanning imager (which uses a narrow line beam or a broad line beam (e.g., a linear slit of predefined width) to scan a sample one line at a time). In the field of fundus imagers, the line scanning imager may be termed a line scanning ophthalmoscope, and includes both the line-scanning laser imager/ophthalmoscope, LSLO (which typically uses a laser to produce a very narrow traversing line across a sample as it scans), and the broad-line scanning (fundus) imager/ophthalmoscope, BLFI, (which may use a non-coherent light source to produce a traversing broad line (or slit) of predefined width across a sample as it scans). Hereinafter, the term line scanning imager may be understood to refer to both of a laser-line (or very narrow-line) scanning imager (e.g., LSLO) and a broad-line scanning imager (e.g., BLFI).

Scan imagers generally capture scattered light returning from each scanned position of a sample (e.g., by use of a collector, e.g., photodetector or photosensor) and montage together the captured scanned positions to create a composite image of the sample, which may define a full-frame (e.g., full field-of-view, FOV) image. For ease of discussion, embodiments of the present invention describe the use of scan imagers to image the fundus of an eye, which is the interior surface of the eye opposite the eye lens (e.g., crystalline lens) and may include the retina, optic disc, macula, fovea, and posterior pole. That is, the present scan imagers may be presented within the context of a fundus scan imager, but it is to be understood that the present invention may likewise be used in scan imagers optimized for other uses, e.g., to image samples other than an eye.

Each type of scan imager has its advantages and disadvantages, and may be optimized for various uses. For example, the confocal point scanning imager inherently avoids defocused light, but since each imaged point (e.g., each captured scanned position) may correspond to one image pixel, it needs to be scanned laterally and vertically across a sample to construct a composite, full-frame image. This may lead to comparatively long image capture times. The line scanning imager generally achieves a measure of confocality in its width direction (perpendicular to the length dimension of the traversing scan line, or line beam) and can be scanned across a sample more quickly than the point scanning imager. However, at least in the case of the broad-line scanning imager, a captured image may not achieve a desired brightness if the scanning, line beam is too narrow. Nonetheless, the broad-line scanning imager can avoid the need for a laser source, making it more cost effective than the other two scan imagers, and can further create a scanning, line beam of varying widths so as to increase the amount of light applied to a scanned sample during each capture sequence and thus produce brighter images, but at the cost of reduced confocality.

When a scan imager is used to image the fundus, it is generally desirable to avoid collecting (e.g., capturing or imaging) extraneous light, as well as reflexes from the cornea and light scattering from the eye lens (e.g., such as due to cataracts). The sequential illumination and collection of individually targeted scanned positions of the retina/fundus, inherent to scan imagers, reduces the collection of unwanted light from extraneous (e.g., peripheral) regions of the fundus, but the elimination/reduction of unwanted reflexes and light scattering from the eye may require a more direct approach. Reflexes from the cornea and light scattering from the eye lens arise from the scan beam traversing the cornea and eye lens as it enters the posterior of the eye. These issues may be addressed by a technique known as pupil splitting, which blocks reflexes from the cornea and light scattering from the eye lens by providing different paths at optimally chosen regions of the pupil for the scan beam entering the eye and for the returning (scattered) light exiting the eye. For example, these regions may be chosen to avoid pupil clipping (e.g., part of a light beam being blocked by the iris whose center defines the pupil), light scattering from cataracts (e.g., clouded regions of the eye lens), and specular reflections (e.g., reflexes) of illumination light (e.g., such as can result from a scan beam impacting the cornea as it enters the eye). In essence, pupil splitting defines a pupil-illumination region (or window) through which the scan beam enters the eye to illuminate a particular scan position on the fundus, and a pupil-collection region (or window) that determines what part of the scattered light exiting the eye is to be collected (by the collector) to capture an image of the scanned position. Pupil splitting may be used in line scanning fundus imagers, but pupil splitting is generally not considered necessary in a confocal point scanning fundus imagers. A side benefit of pupil splitting is that it may tend to maintain the illuminating, scan beam and the returning, scattered light separate not just at the pupil, but also at areas close to the pupil, such as at the eye cornea. The ability for pupil splitting to separate the scan beam from the returning, scattered light may diminish as one moves away from the pupil due to defocusing of the pupil-illumination region and the pupil-collection region.

The above scan imagers may use different radiation sources (e.g., a laser for the coherent point scanning imager and the laser-line scanning imager, and a non-coherent light source such as a lamp or light emitting diode(s), LEDs, for the broad-line scanning imager), but each will generally produce a radiation stream or beam that is conveyed (along a radiation path) to a scanning mechanism/component (e.g., one or more mirror galvanometer (or galvo), MEMS scanners, electro-optical deflectors, and/or rotating polygon scanners). The radiation beam (or illumination beam) output from the radiation source may be shaped by placing a slit (e.g., an aperture of specific configuration) in front of the radiation source. This slit aperture may be imaged to (e.g., a conjugate plane of) the fundus, or to whichever surface is to be imaged. The scanning component receives the radiation beam from the radiation source and creates a scan beam that is scanned in a specified pattern. From the scanning component, the scan beam follows an optic train (that defines a scanning path) to exit the scan imager and scan across the sample (e.g., the eye fundus). This optic train typically includes a scan lens in front of the scanning component (along the scanning path) followed by one or more optics (e.g., lenses or lens structures) that direct the scan beam to the subject to be imaged. In the case of a fundus imager, the lens closest to the eye (along the scanning path) may be termed an ophthalmic lens, or ocular lens.

A problem inherent with such scan imagers is reflexes (e.g., light reflections) at system lenses (or other optics) internal to the scan imager along an illumination and/or collection path of the scan imager. The present invention provides a method, system, or device for eliminating (or diminishing) reflexes at one (or more) target optic (e.g., system optic) within a scan imager. In the case of fundus imagers, reflexes at the lens closest to the eye (e.g., the sample being imaged) are typically of concern, and some embodiments are herein presented within the context of eliminating reflexes at the lens closest to the eye (e.g., the ophthalmic lens), but it is to be understood that the present invention may be applied to another target lens (or other target optic) within the scan imager.

In embodiments, a radiation block (e.g., an illumination block or radiation-blocking component or beam block) imaged to the ophthalmic lens (or other system, target optic at which reflexes are to be eliminated/reduced) is placed between the radiation source and the scanning component to partially block the radiation beam received by the scanning component. A radiation block, or beam block, may be constructed using a foil or metal plate with an opening, a light filter, other light blocking mechanism that selectively blocks part of a light beam while letting other parts through. The radiation block may be at a conjugate plane of the ophthalmic lens and creates a non-radiation zone (non-illumination zone) that is scanned (e.g., moved) across the ophthalmic lens as the scanning component scans the radiation beam from the radiation source. This non-illumination zone creates a moving region of no (or reduced) reflexes on the ophthalmic lens adjacent to the scan beam produced by the scanning component. In embodiments, the radiation block may be placed in front of the radiation source, e.g. in front of the slit aperture of the radiation source. If a pupil splitting optic is positioned in front of the radiation source, then the pupil splitting optic may be placed between the illumination-block and the scanning component. As it would be understood, the illumination block may be substantially imaged to the ophthalmic lens, the pupil splitting optic may be substantially imaged to the eye pupil (or cornea), and the slit aperture may be substantially imaged to the fundus (or retina).

In embodiments, another radiation block (e.g., a collection block or collector-blocking component) may also be imaged to the ophthalmic lens (or to another system, target optic where reflexes are to be eliminated/reduced) and may be placed on an optical path from the scanning component to the collector. The collection block may be located at a conjugate plane of the ophthalmic lens and create a non-collection zone on the ophthalmic lens that is scanned (e.g. moved) across the ophthalmic lens adjacent to the (scattered) returning light from the eye that is headed to the collector. A part of the scattered radiation (e.g., light) returning from the fundus (e.g., sample) may thus be blocked by the non-collection zone creating a second moving region of no (or reduced) reflexes on the ophthalmic lens (or other target optic). In some embodiments, reflexes on the ophthalmic lens may further be reduced by arranging the non-collection zone to partially overlap with the non-illumination zone as they move in tandem on the ophthalmic lens. The collection block may be placed in front of the collector. If a collection aperture (e.g., a pinhole or slit through which light enters the collector) is placed in front of the collector, then the pinhole may be placed between the collector and the collection block. In this case, the collection aperture may be imaged to the fundus (or retina) of the eye, and the collection block may be imaged to the ophthalmic lens (or other target optic). The collector may also be imaged to the fundus, in which case, the collection aperture may be slightly out of focus on the retina.

The present invention may be implemented as part of a confocal point scanning imager or a line scanning imager. A point confocal scan imager, such as a (fundus) confocal scanning laser ophthalmoscope (cSLO), may use a laser (or other bright, confocal light source) to illuminate, and image, a small point (or spot) of the retina at a time.

Figure 2:
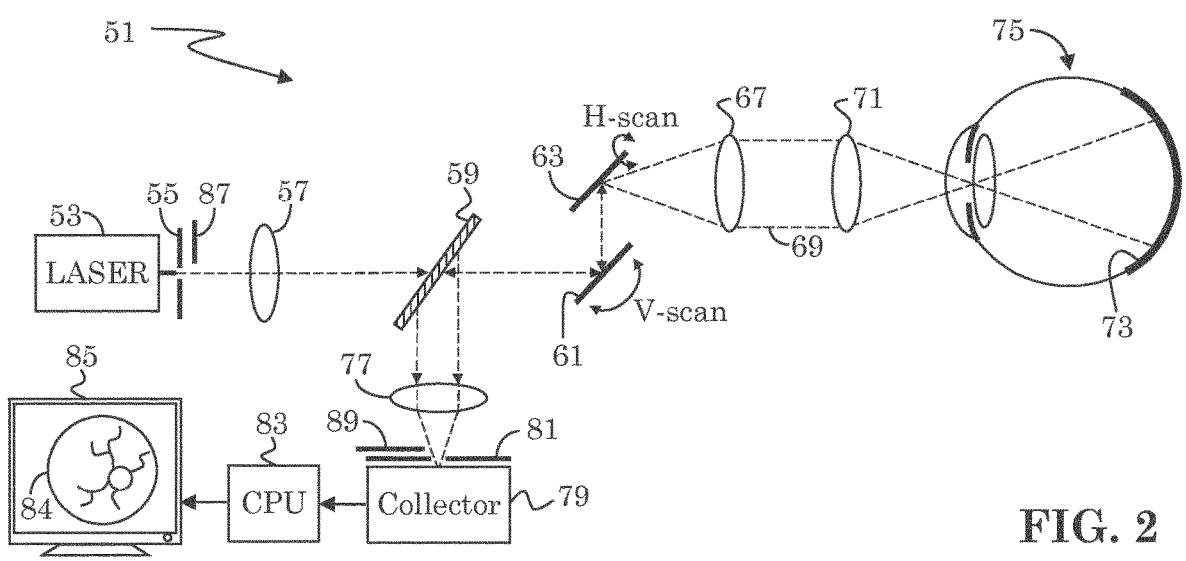
FIG. 2 illustrates a generalized confocal point scanning fundus imager.

FIG. 2 illustrates a generalized confocal point scanning fundus imager 51. A laser or other light source such as a superluminescent diode, SLD, (e.g., radiation source) 53 emits a spatially coherent point beam of light through an optional aperture 55 and a collimating lens 57 through a beam splitter 59 to a scanning component, which in the present example includes two galvanometers 61 and 63 (e.g., servo controlled rotating (or oscillating) mirrors). The first galvanometer (galvo) 61 may provide vertical scanning (e.g., V-scan) of the point beam (e.g., provides scanning in a Y-axis direction that may define columns of illuminated points on a sample to be imaged), and the second galvo 63 may provide horizontal scanning (e.g., H-scan) of the of the point beam (e.g., provides scanning in an X-axis direction that may define rows of illuminated points on the sample). For example, the H-scan galvo 63 may rotate a mirror to scan a point beam horizontally in discrete steps (or in continuous, definable steps) to define a row of points. Once a row of points is completed, V-scan galvo 63 may rotate its mirror vertically to move the scan beam to a new, vertically offset position in preparation for scanning a new row. In an optical path between the scanning component and an eye 75, is a scan lens 67, whose function generally is to receive the scan beam from H-scan galvo 63 at any of multiple scan angles (incident angles), and produce a scan beam 69 with a substantially flat surface focal plane (e.g., a collimated light path). Scan beam 69 may then be focused by ophthalmic lens 71 onto the retina 73 of eye 75 to image the fundus. Scattered light exits eye 75, and returns through ophthalmic lens 71, scan lens 67, and galvos 61 and 63 to reach beam splitter 59. Because the return path of scattered light from eye 75 is similar to the scan beam, galvos 61 and 63 have the effect of "descanning" (or un-scanning) the returning light so that it is a steady beam (non-scanning) by the time it reaches beam splitter 59. At beam splitter 59, the returning light is directed onto another focusing lens 77, which focuses the returning light beam onto a photodetector 79 through a pinhole 81, which may be optically conjugated to the retina 73 and helps to eliminate out-of-focus signal (light). Each illuminated point is imaged (e.g., captured or detected) separately by the photodetector 79, and as the point beam from the scanning component is scanned in a raster pattern across the sample, a series of imaged points are collected to construct a composite image of the retina 73. That is, the signal (e.g., point of light) that is detected by the photodetector 79 may be processed by a computer, or CPU, 83 to form a confocal (full frame) image 84. The resulting confocal image 84 may be displayed on a video display 85, or stored for further processing. An example of a point confocal scanning system integrated within an optical coherence tomography system is provided in U.S. Pat. No. 8,783,868, assigned to the same assignee as the present invention and herein incorporated in its entirety by reference.

As is described in further detail below, optionally, an illumination block 87 imaged to the ophthalmic lens 71 may be positioned in front of the radiation source 53 to create a moving non-illumination zone on ophthalmic lens 71 adjacent the scan beam output from the scanning component (e.g., output from galvo 63). The non-illumination zone prevents (or reduces) reflexes due to the scan beam. Similarly, a collection block 89 may optionally be positioned in front of photodetector 79, and the location of the collection block 89 is chosen such that the optics in the system form an image of collection block 89 at the location of a surface of the ophthalmic lens 71 (e.g., collection block 89 is located at a conjugate plane to a surface of the ophthalmic lens 71) to create a moving non-collection zone on ophthalmic lens 71 that prevents (or reduces) reflexes due to returning, scatter light from the eye 75.

Figure 3:
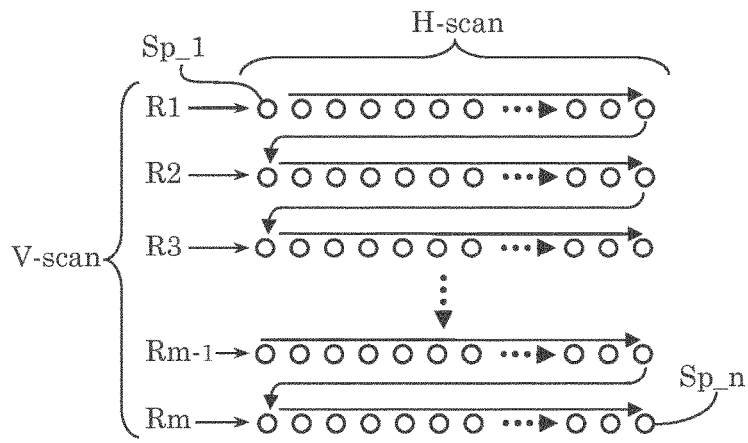
FIG. 3 illustrates a simplified, exemplary scanning pattern for a confocal point scanning fundus imager (or more generally, a point confocal scanning system).

FIG. 3 illustrates a simplified, exemplary scanning pattern of a confocal point scanning fundus imager (or more generally, a point confocal scanning system). It is to be understood that other scanning patterns are possible. In the present, illustrative example, each point Sp_1 to Sp_n is captured separately and individually in a scanning pattern. Since only one point in the sample is illuminated and captured at a time, imaging typically requires scanning over a regular raster (e.g., a rectangular pattern of parallel scanning lines) on the specimen, e.g., the retina, or fundus. For example, a laser scan beam may be scanned across the sample in an X-Y plane (perpendicular to a primary axial direction (e.g., Z-axis) of the scan beam) by using a scanning component (e.g., galvos 61 and 63). A separate row (e.g., R1 to Rm) of points may be captured in corresponding separate horizontal scans, H-scan, one after another, and the scan beam may be scanned vertically in one-row-offset incremental steps (e.g., one vertical step after each horizontal scan) to define a vertical scan, V-scan. Typically, slower scans may provide a better signal-to-noise ratio, resulting in better contrast and higher resolution.

Due to the point confocal arrangement of illumination and detection, confocal scanning imagers may advantageously suppress stray-light and out-of-focus light, and thereby produce high contrast images without the need for pupil splitting. However, since they operate with point illumination, they may require high intensities which raise safety issues when imaging a retina. Similarly, since much of the light from a sample is blocked at pinhole 81, their increased resolution is generally at the cost of a decrease in captured signal intensity so that exposure time may need to be elongated. Additionally, the confocal point scanning fundus imager generally requires multiple scanning mechanisms to achieve horizontal and vertical scans (e.g., galvo 63 for horizontal scanning and galvo 61 for vertical scanning), which can be expensive and complicated, and can slow their image production since many points need to be collected to construct a full-frame composite image. This also may raise issues of eye movement during the construction of an image, which may lead to image distortions.

The line scanning imager differs from a confocal point scanning imager by using a line beam that traverses a certain width-span of the sample instead of a point beam. Consequently, the line scanning imagers may capture an entire row (or column) of image data at a time and require a more simplified scanning component (e.g., one less galvo than the confocal point scanning fundus imager described above). In some embodiments, line scan imagers may still include a second scanner to allow for imaging over a wider field of view than the line. Alternatively, the entire optics head of the system can be rotated manually to allow for illumination over the wider field of view.

Figure 4:
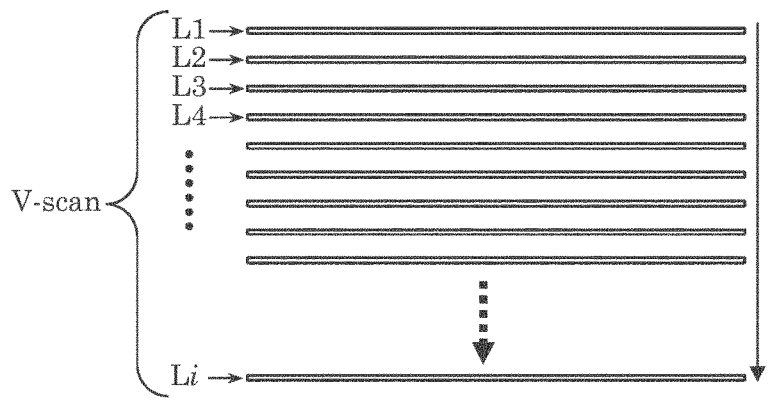
FIG. 4 illustrates a simplified, exemplary scanning pattern for a line (confocal) scanning system.

FIG. 4 illustrates a simplified, exemplary scanning pattern for a line scanning system. In the present example, a traversing line beam is produced by a radiation source (not shown) and scanned vertically (e.g., by use of a vertical scanning galvo, such as galvo 61 of FIG. 2) to produce multiple scan lines L1 to Li in a vertical scan pattern, V-scan. As explained above, two types of line scanning imagers are the laser-line scanning imager and the broad-line scanning imager. For ease of discussion, scan lines L1 to Li may represent line scans as produced by a laser-line scanning imager or broad-line scanning imager, with the understanding that scan lines produced by a laser-line scanning imager are typically much more narrow than those produced by a broad-line scanning imager. Line scanning imagers, in general, may maintain some level of confocal suppression of out of focus light perpendicular (e.g., along the Y-axis in FIG. 4) to the scan line (L1 to Li), but lack confocal suppression along the line (e.g., along the X-axis in FIG. 4). Line Scanning systems have been combined with pupil splitting (see for example Muller et al. U.S. Pat. No. 8,488,895, which is herein incorporate in its entirety by reference). Advantageously, a line scanning imager can scan faster across the retina (or fundus) than a confocal point scanning imager, and is therefore less sensitive to motion artifacts, but at the expense of less out of focus suppression. However, variations in line intensity or linear array sensitivity in a line scanning system may lead to streaking in a captured image.

The broad-line scanning imager strives to combine some of the benefits of a laser-line scanning imager with those of a flood illumination imager. The broad-line scanning imager uses broad lines (or slits) of illumination much broader than those of a laser-line scanning imager, and may therefore have a much larger etendue, enabling the use of non-coherent light sources (e.g., non-laser sources), such as a lamp(s) or LED(s), which are typical less expensive and can provide broad band illumination that may help to achieve a more natural looking image.

Figures 5A, 5B, 5C:
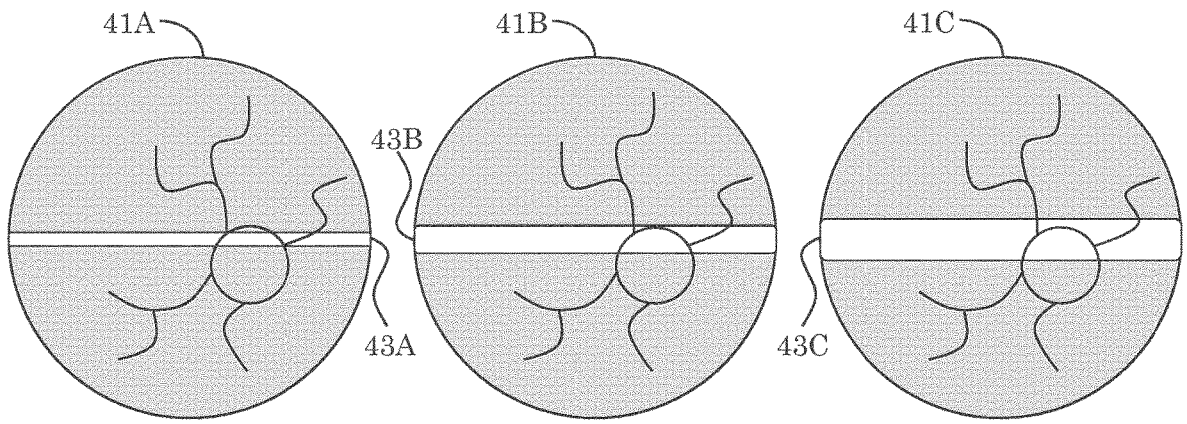
FIGS. 5A, 5B and 5C each illustrate a differently sized, exemplary illumination broad lines (or slits) of different widths, such as may be used with a line scanning fundus imager.

FIGS. 5A, 5B and 5C each illustrate a differently sized, exemplary broad line (or illumination slit) 43A, 43B, and 43C for illuminating a respective fundus area 41A, 41B, 41C. In each of FIGS. Illumination slits 43A, 43B, and 43C are illustratively shown as being of different widths. Each illumination slit 43A, 43B, 43C corresponds to the location of a scan beam on the fundus at a particular scanning step or time. Note that the scan beam can be scanned either smoothly across the retina, or moved in steps. Increasing the width of an illumination slit, such as slit 43C versus strip 43A, increases the amount of light applied and may provide an improved dynamic range. The sharpness of the edge of the illumination strip can be used to find an optimized focus for the line scanning system for the case where the illumination has not moved significantly during an acquisition by the detector (typically when the scan beam is being scanned in steps and is relatively motionless during an acquisition). Various image processing techniques may further be used to improve a constructed image. For example, locations on the retina that are not illuminated can be detected (e.g., image captured) to evaluate background levels, e.g., stray light levels, coming from out-of-focus regions of the eye, and this background level may then be subtracted from a captured line image, e.g., from illumination slits 43A, 43B or 43C. Also, the size of each vertical scan step may be made smaller than the width of an illumination slit, such that multiple consecutive illumination slits cover the same region of a retina. In this manner, multiple image captures will image the same region of the retina. This permits the use of various image processing techniques (e.g., averaging) to improve the image quality of an individual region. Alternatively, one may select the best image quality of an individual region for montaging into the final composite image. Furthermore, multiple pupil splitting configurations may also be used with a broad line imaging system. For example, pupil splitting for illumination and detection may be achieved nearer to the cornea than is typical for flood illumination fundus imagers, and instead of illuminating an annular ring (as describe above in reference to a flood illumination fundus imager), a slit may be illuminated. Examples of broad line (slit) scan imagers are provided in U.S. Pub. No. 2017/0049323 and U.S. Pub. No. 2018/0014727, both assigned to same assignee as the present invention and both herein incorporated in their entirety by reference.

The above described (fundus) scan imagers may use various scanning configurations. For illustration purposes, some simplified scanning configurations are presented here within the context of a line scanning imager (e.g., an imager using a scanning line beam), but the configurations may also be applied to point scanning imagers, as it would be understood by one versed in the art.

Figure 6A:
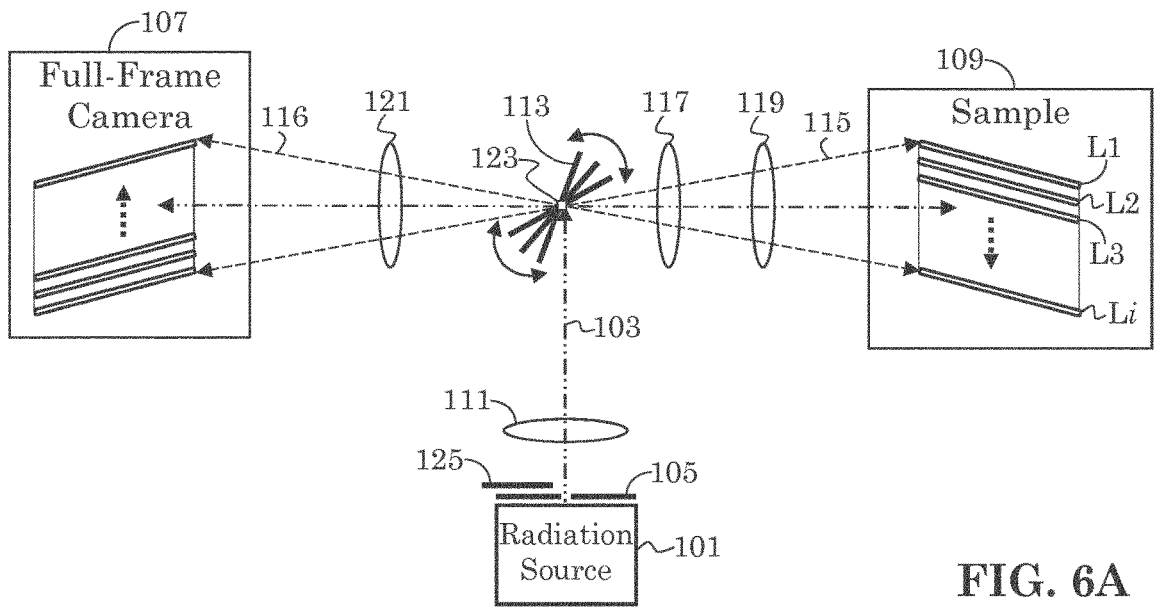
FIG. 6A illustrates an idealized scan configuration of a so-called "scan-non-descan" system, wherein a traversing line beam illuminates a line across a sample as it is scanned (see for example, FIGS. 4, 5a, 5B, and 5C), and returning reflected/scattered light is permitted to similarly scan across a collector (e.g., a photodetector or camera), which may optionally be coupled to a CPU for further processing and to a monitor for display, as illustrated in FIG. 2.

FIG. 6A illustrates a scanning configuration (a so-called "scan-non-descan" system) wherein a traversing line beam 115 illuminates a line (e.g., narrow line or broad line) L1 to Li traversing a sample 109 in one dimension (e.g., X-axis) as the line beam 115 is scanned in another dimension (e.g., Y-dimension), such as illustrated in FIGS. 4, 5A, 5B, and 5C. The returning (e.g., reflected or scattered) light 116 is permitted to likewise scan across a collector 107 (e.g., a photodetector or camera), which may optionally be coupled to a CPU for further processing and to a monitor for displaying a full-frame image, as illustrated in FIG. 2. In the present example of FIG. 6A, collector 107 may be a full-frame digital camera and the returning light 116 may "paint" a full-frame image as it scans across a two-dimensional (2D) photosensor (e.g., a 2D array of photodetectors) of the camera. That is, each detected line of returning light 16 may be captured at a different location on the camera, buffered, and processed to construct a composite full-frame image, either with a single acquisition for the full-frame image, or through multiple acquisitions (e.g. moving the series of line illuminations to additional horizontal locations on the sample) that make up the full frame. A radiation source 101 (e.g. light source, such as a laser, lamp, or LED) produces an illumination line beam 103 (non-coherent light beam or laser beam). A radiation aperture 105, imaged to the sample 109 (e.g., surface that is to be imaged), may be placed in front of radiation source 101 to help shape the illumination line beam 103. In the case of a fundus scan imager, radiation aperture 105 may be imaged to the retina of an eye. Illumination line beam 103 may pass through one or more optics (e.g., a lens) 111 before reaching a scanning component (e.g., galvo mirror) 113, which creates a scanning line beam of radiation (e.g., scanning line beam 115) that defines illumination lines L1 to Li across sample 109. It is to be understood that in a more practical application, scanning line beam 115 output from scanning component 113 may pass through a scan lens 117 and ophthalmic lens 119, as described above in reference to FIG. 2, before reaching the sample 109 (e.g., a retinal, or fundus, of an eye). In the present example, line beam 115 output from scanning component 113 is scanned vertically (e.g., Vscan as illustrated in FIG. 4) in steps along the sample 109. Scattered light 116 returning from the sample 109 may pass through an aperture 123 in scanning component 113 (or otherwise conveyed from sample 109) to collector 107, and may likewise scan vertically in corresponding steps on the collector 107. A more practical application may include a focusing lens 121 in front of the collector 107. In the case of a fundus scan imager, scanning component 113 may be substantially optically conjugate with the pupil of the eye.

As is described in further detail below, an illumination block 125 imaged to a target optic (e.g., ophthalmic lens 119) may be positioned in front of the radiation source 101 to create a moving non-illumination zone on the target optic, which may be adjacent the scan beam 115 output from the scanning component 113. This non-illumination zone prevents (or reduces) reflexes due to the scan beam 115.

Figure 6B:
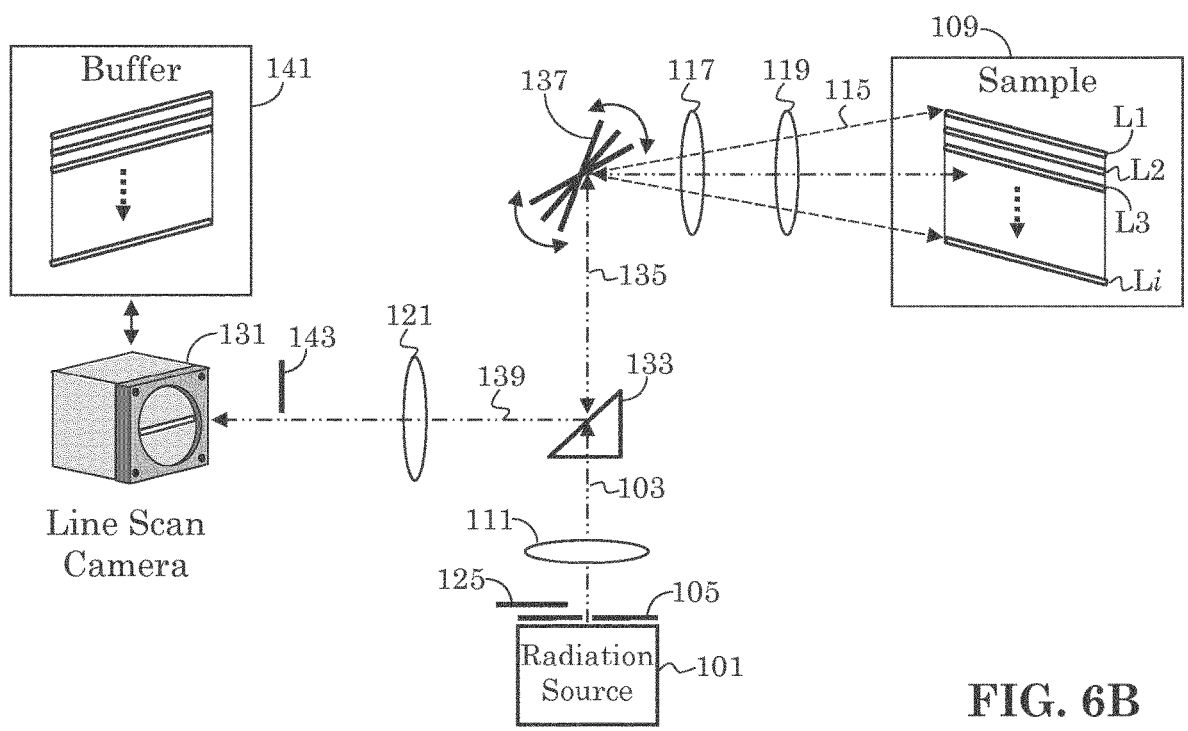
FIG. 6B illustrates an idealized scan configuration of a so-called "scan-descan" system, wherein a line beam is scanned across a sample, but a line of returning scattered light is maintained at a single, predefined position on the collector and not scanned across the collector.

FIG. 6B illustrates an idealized scan configuration of a so-called "scan-descan" system, wherein a scanning line beam 115 is scanned across a sample 109, but a line of returning scattered light 139 is maintained at a single, predefined position on the collector and not scanned across the collector. All elements in FIG. 6B similar to those of FIG. 6A have similar reference characters and are described above. Because the returning line of scattered light 139 is not scanned, this scan configuration permits the use of a line-scan camera 131 as the collector. Alternatively, a full-frame digital camera with a line, e.g., row of pixels, (or a predefined number of pixel rows to define a broad line) within its 2D array is designated a region-of-interest, ROI, and the designated ROI is used to receive and capture the returning light 139. In the present example, radiation source 101 produces a line (or broad line/slit) of illumination (e.g., line beam) 103, which passes through a beam splitter (or beam divider) 133 onto optical path 135 to reach scanning component (e.g., galvo mirror) 137. Scanning component 137 converts the received illumination beam into a scan beam that scans across sample 109. As stated above, in a more practical application, light from scanning component 137 may pass through a scan lens 117 and an ophthalmic lens 119 before reaching the sample 109 (e.g., retinal, or fundus, of an eye). In the present example, scanning component 137 may scan the scan beam 115 vertically in discrete scan steps along the sample, but other scanning orientations may be used. At each scan step, light is reflected/scattered back (in a capture phase) to scanning component 137. For purposes of discussion, scanning component 137 may be assumed to be substantially stationary during this capture phase, and so reflects the returning light along the same optical path 135 as the incident light from radiation source 101. Therefore, optical path 135 may be termed a shared path, as illustrated by dual-headed arrows. The returning, stationary line of scattered light is directed by beam splitter 133 onto a collection path 139, which conveys it to a photodetector, e.g., line-scan camera 131. As shown, the location of returned scattered light on collection path 139 is substantially stationary irrespective of the vertical scan position of a line beams L1 to Li on sample 109, which is herein termed a "descan" operation. This permits the use of line-scan camera 131, which may contain a single row of pixels used to capture data very quickly (e.g., using fast CCD sensors or CMOS image sensors). The captured light from each discrete scan step may be captured and mapped to a buffer 141 at a position corresponding to the scan position of the corresponding scan line L1 to Li. The buffered line images may then be reconstructed (e.g., montaged or stitched) into a full frame image, such as by use of a CPU (e.g., computing system or device) and rendered on a computer display, as illustrated in FIG. 2.

Optionally, an illumination block 125 may be used to reduce or eliminate reflexes at a target optic. Illumination block 125 may be positioned in front of the radiation source 101 and may be placed at a conjugate plane of the target optic (e.g., scan lens 119). Because of the scanning action of scanning component 137, a moving non-illumination zone is created on the target optic, which may be adjacent the scan beam 115 output from the scanning component 137. The non-illumination zone prevents (or reduces) reflexes on the target optic due to the scan beam 115. Also optionally, a collection block 143 imaged to the same target optic may optionally be positioned in front of the collector (e.g., line-scan camera 131). Use of collection block 143 is facilitated due to the returning scattered light on collection path 139 being relatively steady (e.g., not scanning) Consequently, a moving non-collection zone may be created on the target optic (e.g., ophthalmic lens 119) that prevents (or reduces) reflexes due to light returning from the sample 109. The non-collection zone and non-radiation zone may abut or overlap each other as they move at a conjugate plane of, or directly on, the target optic.

Further reduction of reflexes may be achieved through the use of cross polarizers. That is, introducing two polarizers orthogonal to each other in a cross polarizer configuration, e.g., one in each of the illumination and detection (collection) paths may further reduce reflexes. For example a first polarizer may be positioned in the illumination path and a second polarizer in an orthogonal state (e.g., rotated 90 degrees relative to the first polarizer) may be positioned in detection path. The polarizers could be anywhere in these paths, but a preferred embodiment could have them in the stationary portions of the paths, e.g., the first polarizer could be positioned prior to the scanning mirror 137 in illumination path from the light source 101 to the sample 109 (e.g., the eye), and the second polarizer could be positioned in the collection path 139 following the scanner 137 (e.g., in descanned portion of the optical (collection) path from the sample (e.g., eye) to the collector).

Figure 6C:
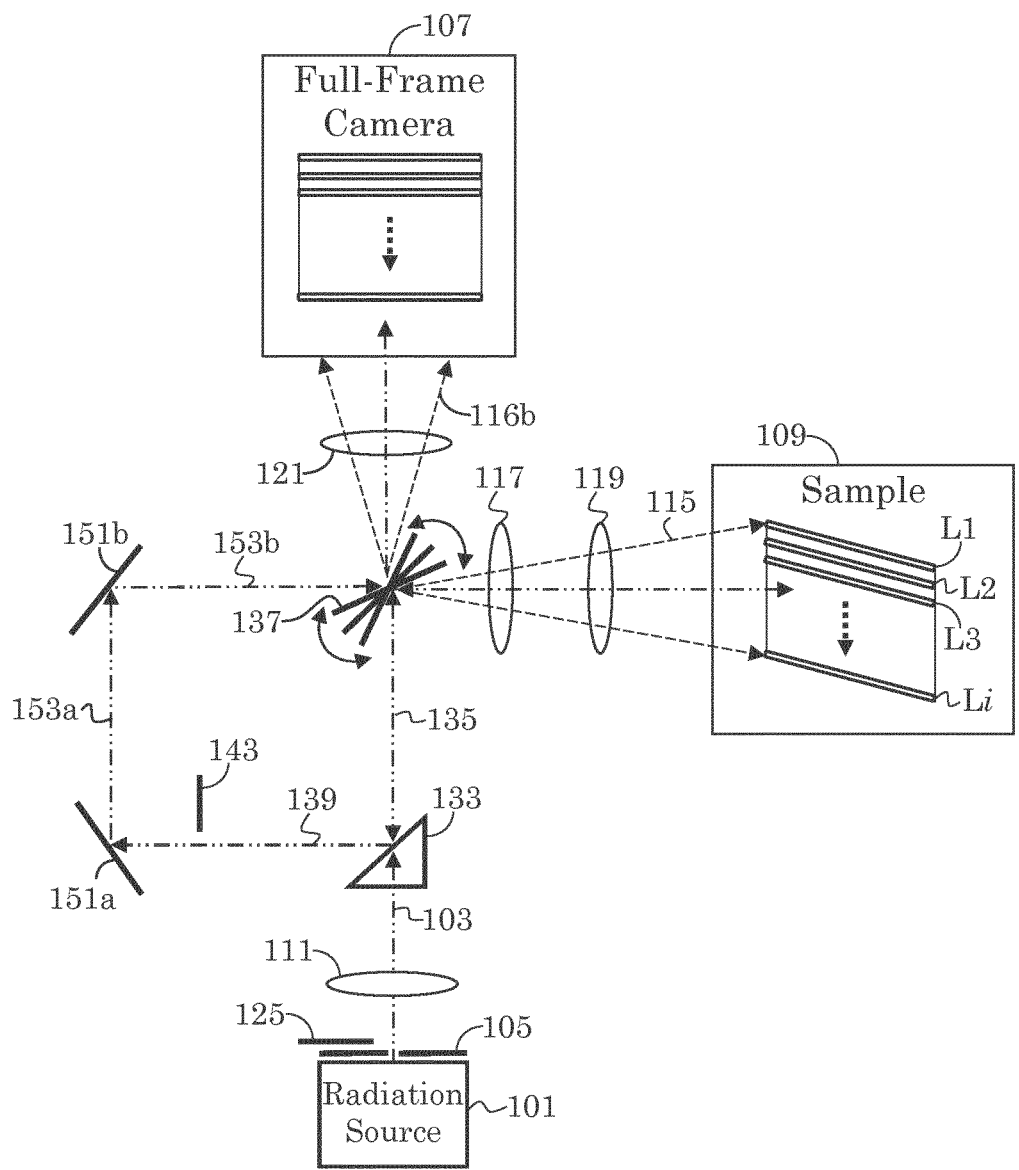
FIG. 6C illustrates an example of a so-called scan-descan-rescan system, wherein a secondary scanning mechanism is incorporated into a scan-descan system so as to scan anew (e.g., rescan) the otherwise non-scanning, returning, scattered light produced by a scan-descan system before it reaches the collector, and thereby scans anew the returning scattered light across the collector. Optionally, this rescan functionality can be provided either by a second scanning component, or by a different part of the scanning component that scans the scan beam across the sample. For example, rescanning may be accomplished by using the back side of, or a different location on, a single scanning component that also scans the scan beam across the sample.

Some of the benefits of the scan-non-descan system of FIG. 6A, such as simplified image capture architecture, and the scan-descan system of FIG. 6B, such as the non-scanned, steady, returning light that facilitate the use of collection block 143, may be achieved in a third scanning configuration, which is herein termed "scan-descan-rescan". FIG. 6C illustrates a simplified scan-descan-rescan system, wherein a secondary scanning mechanism may be incorporated into a scan-descan system so as to scan anew (e.g., rescan) the otherwise non-scanning (e.g. descanned), returning, scattered light produced by the scan-descan system before it reaches the collector, and thereby scans anew the returning scattered light across the collector. All elements in FIG. 6C similar to those of FIGS. 6A and 6B have similar reference characters and are described above. As before, a radiation source 101, with optional aperture 105 and collimating lens 111, creates an illumination line beam 103 that passes through beam splitter 133 onto optical path 135 to reach scanning component (e.g., galvo) 137. Scanning component 137 converts the received illumination beam into a scan beam of (e.g. scanning line beam 115) that may pass through a scan lens 117 and an ophthalmic lens 119 to scan across a sample 109 (e.g., retinal, or fundus, of an eye). As in the case of FIG. 6B, light returning from sample 109 is descanned by scanning component 137 to create a substantially steady, returning line beam on optical path 135, which is directed by beam splitter 133 onto collection path 139. At this point, the descanned, returning light on collection path 139 may be directed, such as by use of one or more mirrors 151a/151b along optical paths 153a and 153b to a second scanning mechanism. In the present example, the back of the galvo (scanning component 137) is reflective and used as the second scanning mechanism in order re-scan the returning light, and define a re-scanned collection beam 116b on collector 107, via focusing lens 121. Since the scan beam 115 and re-scanned collection beam 116b are defined together by scanning component 137, they correspond to each other.

As in the case of FIG. 6A, illumination block 125 may be used to reduce or eliminate reflexes at a target optic, such as ophthalmic lens 119. That is, illumination block 125 may be positioned in front of aperture 105 and radiation source 101, and be imaged to the target optic (e.g., to the back surface or front surface of the target optic). This creates a moving non-illumination zone on the target optic, which may be adjacent the scan beam 115 output from the scanning component 137. Additionally, collection block 143 may be used prior to the re-scanning of the returning light that defines re-scanned, collection beam 116b. That is, collection block 143 may optionally be positioned along any of optical paths 139, 153a, or 153b. As in the case of FIG. 6B, collection block 143 may be imaged to the same target optic where reflex reduction due to returning scattered light is desired. Use of collection block 143 is facilitated due to the returning light between it and beam splitter 133 being relatively steady (e.g., not scanning) on a collection path (e.g., 139, 153a, and/or 153b). Consequently, a moving non-collection zone may be created on the target optic (e.g., ophthalmic lens 119) that prevents (or reduces) reflexes due to returning light from the sample 109. As before, the non-collection zone and non-radiation zone may abut or overlap each other as they move at a conjugate plane of, or directly on, the target optic.

Additional examples of scanning configurations used in fundus scan imagers are provided in U.S. Pat. No. 9,549,672, assigned to the same assignee as the present application and herein incorporated in its entirety by reference.

Generally, lenses may introduce aberrations due to their focus not being perfect (e.g., light may be spread out over some region of space rather than focused to a point). For example, light from the outer portion/edge of a lens may tend to be blurred or distorted as compared to the inner portion of the lens. This type of aberration may be due to field curvature, and may arise from the tendency for lenses to focus an image a little too close at the edges as compared to the center, where the focus is best. Optionally, one or more spherical mirrors may be used to cancel/counteract/reduce this type of aberration. The field curvature over multiple lenses may be tracked (e.g., combined) by use of the Petzval sum. Generally, converging lenses (e.g., as used in the present exemplary embodiments), have positive terms in this sum, under the consistent conventions for radius that are assumed in deriving the Petzval sum. By contrast, converging mirrors have a negative radius with negative field-curvature, and may herein be used to counter the field curvature of the converging lenses. Although multiple spherical mirrors may be used (e.g., one in the illumination path from the light source to the eye and another in the return viewing path (e.g., collection path) from the eye to the collector), one spherical mirror (e.g., sized to counter the combined field curvature of the lenses according to the Petzval sum) may suffice, and the one spherical mirror may be positioned anywhere along the viewing path, either in the shared, scanned, or descanned segments.

A benefit of using a spherical mirror in the shared path (e.g., the portion of the optical path shared by the illumination light and the returning collection light) is that a primary challenge in fundus imaging is blocking the back-reflections from the cornea and optics in the portion of the optical system that is shared by the illumination and collection paths (e.g., between the splitting mirror and the retina). Unlike a transmissive lens, where the light is passing through the interface between air and glass, a mirror has no significant back-reflection, greatly reducing the issue of back-reflections. A difficulty with replacing lenses in the shared path with mirrors is that the mirrors reflect light, thus folding the optical path back towards the human eye, which may create difficulties with mechanical interference between the optical system and the human face.

Figure 6D:
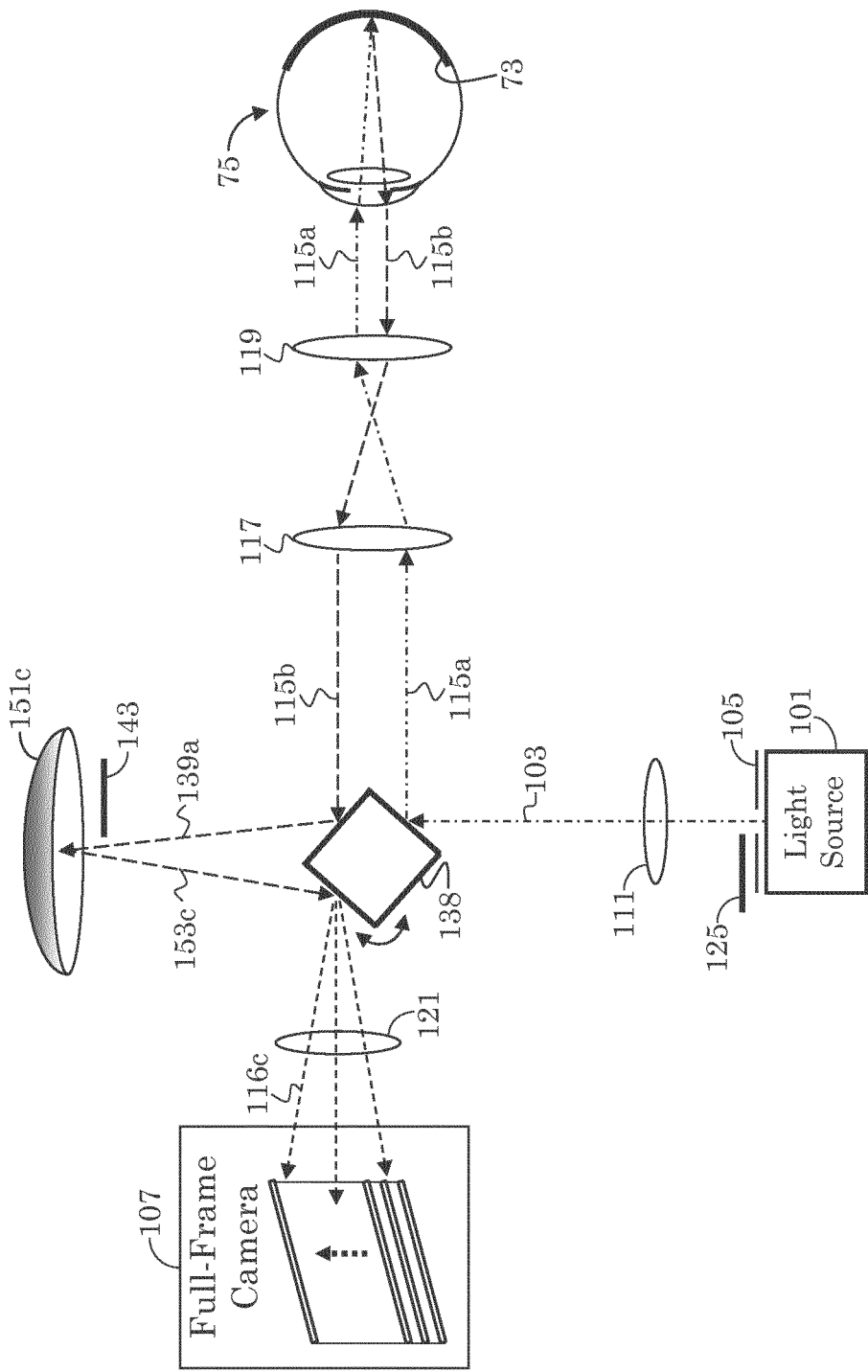
FIG. 6D shows the integration of a spherical mirror into a scan-descan-rescan system similar to that of FIG. 6C.

A spherical mirror may be used with any of the scanning configurations discussed herein, but for illustrative purposes, FIG. 6D shows the integration of a spherical mirror into a scan-descan-rescan system similar to that of FIG. 6C. All elements in FIG. 6D similar to those in FIGS. 2, 6A, 6B, and 6C have similar reference character and are described above. As in the example of FIG. 6C, a radiation source 101, with optional aperture 105 and collimating lens 111, creates an illumination line beam 103, but unlike the example of FIG. 6C, no beam splitter 133 is needed. Instead, illumination beam 103 may directly reach the scanning component, which in the present example is embodied by a block of mirrors (e.g., a polygon scanner) 138 that swivels back-and-forth to achieve scanning across a sample, e.g., eye 75. Thus, polygon scanner 138 converts the received illumination beam 103 into a scan beam (e.g. path 115a) that may pass through a scan lens 117 and an ophthalmic lens 119 to scan across a the retinal 73 of eye 75. Scattered light returning from eye 75 (e.g. light path 115b) is descanned by a different surface of polygon scanner 138 to create a substantially steady, returning line beam on optical path 139a, which is directed to spherical mirror 151c.

A difficulty of using spherical mirrors is that, to stop an optical beam directed at the spherical mirror from reflecting directly back on itself, the beam needs to hit the mirror off-axis (e.g., not perpendicular to the surface of the mirror), but hitting the mirror off-axis may create unwanted astigmatism. There are several ways to address this. To minimize the astigmatism, it is desirable to hit the mirror (e.g., spherical mirror 151c) as on-axis as possible. The astigmatism can be eliminated by adjusting the radius of curvature of the mirror along the plane of reflection of the incident beam. The astigmatism associated with the difference in mirror curvature between the plane of reflection and orthogonal plane then can cancel the astigmatism associated with the off-axis illumination. An alternative approach for canceling the astigmatism of a first spherical mirror (e.g., spherical mirror 151c) is to bounce the beam off a second spherical mirror (not shown) with a plane of reflection that is orthogonal to the plane of reflection at the first spherical mirror. The astigmatism from the two mirrors is then orthogonal and thus cancels. To avoid other aberrations, one could also use parabolic or other higher order shapes for the mirrors.

A benefit of using a spherical mirror in the descanned path is that it may be used to help redirect the descanned path back to scanner 138. As illustrated by mirrors 151a and 151b of FIG. 6C, the descanned path is typically folded by multiple mirrors in order to be returned to scanner 137 and be re-scanned. Since spherical mirror 151c intrinsically folds an optical path (e.g., reflects light), its position in the descanned path permits it to serve two functions. First, it compensates for aberrations due to field curvature of the lenses in the system (e.g., according to the Petzal sum). Secondly, spherical mirror 151c serves the folding function of returning the descanned line beam along optical path 153c to another surface of polygon scanner 138, where it is re-scanned to define a re-scanned collection beam 116c on collector 107, via focusing lens 121. Optionally, adding a second spherical mirror in the illumination path (e.g., path from light source 101 to polygon scanner 138) would introduce a second folding path, and folding of the optical paths could make the design more compact, making it possible to reduce the size of the fundus camera.

As before, illumination block 125 may be used to reduce or eliminate reflexes at a target optic (e.g., ophthalmic lens 119). That is, illumination block 125 may be positioned in front of aperture 105 and radiation source 101, and be imaged to (located at a conjugate plane to a surface of) the target optic (e.g., to a curved surface of the target optic) to create a moving non-illumination zone on the target optic. Collection block 143 may be positioned on the descanned segment of the returned path from eye 75. In the present example, collection block 143 is positioned before spherical mirror 151c in the descanned path from polygon scanner 138 to spherical mirror 151c. Optionally, collection block 143 may be imaged to (located at a conjugate plane to a surface of) the same target optic (e.g., ophthalmic lens 119), or to another target optic, where reflex reduction due to returning scattered light is desired. Consequently, a moving non-collection zone may be created on the target optic that prevents/reduces reflexes due to returning light from the retinal of the eye 75. The non-collection zone and non-radiation zone may abut or overlap each other as they move on the target optic, or at a plane conjugate to the target optic.

As is discussed above, the present invention addresses the reduction of image artifacts, such as those caused by reflexes from system optics in a scan imager, such as a line scanning imager or point scanning imager. This may be achieved by minimizing or eliminating an overlap between illumination and collection optical paths on a given optic component (e.g., a target optic) through the placement of light blocks (e.g., radiation block, illumination block, or collector block) in the illumination and/or collection paths at a conjugate plane to the target optic (e.g., the plane to which the target optic is imaged). As is explained above, the present technique may be applied to different scanning configurations of a scan imager. For illustration purposes, some specific examples of a scan-descan scan imager are provided below, with the understanding that the present discussion may be applied to other scanning configuration, unless otherwise specified. As is explained above, in a scan-descan configuration, scattered light returning from a sample is descanned, resulting in the returning light in at least part of the collection path being stationary (e.g., not scanning). An illumination block may be inserted in the illumination path, and a collection block may be inserted in the stationary part of the collection path, and images of these two optical blocks (e.g., darken zones) may be created on one or more target optics (e.g., the ophthalmic lens or scan lens), which may eliminate overlap between the illumination and collection paths at the target optic, and thus eliminating collection of reflexes from the target lens. The following examples illustrate various design concepts to make this reflex blocking effect more robust against variations in alignment, focus, etc.

As discussed above, a scan imager minimizes unwanted light returning to the detector (e.g., camera) by illuminating a limited region of a sample to be imaged, e.g. the retina of an eye, at a time and only collecting light from this limited region, thus blocking light that would have been reflected or scattered back into the camera from other illuminated regions of the sample. In line scanning imagers for ophthalmic imaging, separation between illumination and collection at a plane near the eye pupil (pupil splitting) may eliminate reflexes from the eye cornea and reduce reflexes from the ophthalmic lens (the imager lens closest to the cornea), but doesn't eliminate ophthalmic lens reflexes.

In a scan imager, such as a line scanning imager, the scanning component may be imaged to the pupil plane. Therefore, splitting of illumination and collection at the pupil (or close to it, such as at the cornea) can be accomplished relatively easily by splitting the illumination light and the collection light either at the scanning component (e.g., have the separate illumination and collection windows imaged to the scanning component), or just prior to it, which may be close to the cornea plane. That is, if the scanning component is imaged substantially to the pupil, then splitting the illumination and collection windows just prior to the scanning component would place the pupil splitting closer to the cornea.

Separation between illumination light and collection light at the ophthalmic lens (or other target optic in the scan imager), however, is more difficult. Typical methods of reducing reflexes at the ophthalmic lens rely on a combination of pupil splitting at the pupil plane and an (illumination) slit with a highly limited etendue (e.g., very narrow slit requirements), but even this has limited success. In addition to not fully eliminating the ophthalmic lens reflex, relying only on the narrowness of the slit illumination leads to extremely narrow slits (e.g., 0.25 degree widths in practical applications) and/or small scanning steps with overlapping slit illuminations on the retina that increase the number of scans need to complete a full scan pass across the retina (e.g. the subject/sample being imaged). This very narrow, slit width requirement also limits the amount of light reaching the retina and leads to long acquisition times or noisy images.

It is noted that since eye lengths (and pupil sizes) vary, as it would be understood by those versed in the art, it is customary to define linear distance along a span of the retina (e.g., the width of an illumination slit) in terms of degrees, meaning the width size that would result in a field of view spanning the specified degrees at the retina assuming a focal length substantially from the pupil to the retina.

In the present invention, instead of minimizing the narrowness of the slit illumination (e.g. the width of the illumination slit/line beam) to reduce reflexes at the ophthalmic lens, reflexes caused by overlap between the illumination and collection paths at the ophthalmic lens (or another target optic component within the scan imager) is addressed directly, independent of pupil splitting. This may be achieved through the placement of light blocks in the illumination and/or collection paths at a conjugate plane to the ophthalmic lens (e.g., an image plane to which the target optic is imaged), such that the light blocks are imaged to (focused on) the target optic.

FIG. 7 illustrates an alternate scan-descan configuration example of a slit (or line) fundus scan imager incorporating the present invention. Elements in FIG. 7 similar those of FIGS. 2 through 6 have similar reference characters, and are discussed above. Illumination (e.g., a slit, or line, beam) from a radiation (or illumination) source 101 follows an illumination beam path (103a to 115a) through an illumination slit 105, which may help shape the slit beam (or slit illumination), past a first beam block (e.g., illumination block) 125 through a lens 111 to scanning component 137, where it is scanned to produce a scan beam on path 115a. The scan beam may traverse a scan lens 117 and an ophthalmic lens 119 to enter eye 75 and scan incident on the retina 73. Light scattered from the retina 73 returns following a collection beam path (e.g., 115b to 103b to 161) back through ophthalmic lens 119 and scan lens 117, is descanned by rotating scan mirror 137, is deflected by a pick-off mirror 163 onto optical path 161 to pass through lens 121 past a second beam block (e.g., collection block) 143 to a camera 131, e.g., a detector or collector. In the present example, scanning component 137 may be imaged to the pupil plane of eye 75, and pick-off mirror 163 may be positioned close (e.g., just prior) to scanning component 137 to split the illumination and collection path (e.g., provide pupil splitting) closer to the cornea. Also in this example, camera 131 may be a line-scan camera, and may use time delay integration (TDI) to generate the vertical dimension of an image (e.g., a full frame image). As discussed above, line images captured by camera 131 may be buffered, processed by a CPU, and stored for future processing and/or shown on a display (see, for example, FIG. 2). In the present example, ophthalmic lens 119 is the target optic on which reflex artifacts are to be removed, or reduced. Therefore, both beam blocks 125 and 143 may be imaged to the ophthalmic lens 119. In particular, beam blocks 125 and 143 may be imaged to the back surface 119a of ophthalmic lens 119. Alternatively, beam blocks 125 and 143 may be imaged to the front surface 119b of ophthalmic lens 119, or one beam block (e.g., illumination block 125) may be imaged on the back surface of ophthalmic lens 119 (e.g., surface 119b) and the other beam block (e.g., collection block 143) may be imaged to the opposite side surface (e.g., front surface 119a) of the ophthalmic lens 119.

In the present scanning configuration (FIG. 7), where light returning from a sample (e.g., eye 75) is descanned, parts of the illumination and collection paths may be substantially stationary, e.g., an illumination beam output from light source 105 may be stationary on optical path 103a prior to being scanned by scanning component 137, and returning light (e.g., a collection beam) on collection optical paths 103b and 161 may be stationary after being descanned by scanning component 137. Although illumination block 125 may be inserted anywhere in the illumination path (e.g., from 103a to 115a) and collection block 143 may be inserted anywhere in the collection path (e.g., 115b to 103b to 161), for ease of implementation, illumination block 125 may be positioned on a stationary portion of the illumination path (e.g., 103a) prior to being scanned by scanning component 137 and collection block 143 may be positioned on a stationary portion of the collection path (103b and/or 161) after being descanned by scanning component 137.

FIG. 8 provides a simplified, not to scale, and close-up view of the ophthalmic lens 119 of FIG. 7, along with the imaged illumination block 125' (e.g., a non-illumination zone as created by illumination block 125), imaged collection block 143' (e.g., non-collection zone as created by collection block 143), an illumination window 165 through which a scan beam from the scanning component 137 may pass to reach the eye 75, and a collection window 167 through which returning light from the eye 75 may pass to reach the scanning component 137 on is way to the collector 131. That is, illumination block 125 may create an imaged illumination block 125' that defines a non-illumination zone through which a scan beam from scanning component 137 may not pass, and collection block 143 may create an imaged collection block 143' that defines a non-collection zone through which light returning from eye 75 may not pass. As shown, the imaged illumination block 125' may optionally be made to overlap the imaged collection block 143' (e.g., define an overlap zone 169) on the target optic (e.g., the lens closes to the eye 75, or the ophthalmic lens 119). This eliminates any overlap between the illumination path 115a (e.g., illumination window 165) and the collection path 115b (e.g., collection window 167) at this optic, and thus eliminates reflexes from this optic. As the scanning component 137 sweeps (e.g., rotates), the two imaged blocks 125' and 143' move together across the ophthalmic lens (e.g., as illustrated by arrows 171a/171b), maintaining their overlap 169 and thus the blocking of reflexes. Alternatively, illumination block 125' and collection block 143' may be imaged to abut, but not overlap, each other.

Figure 9:
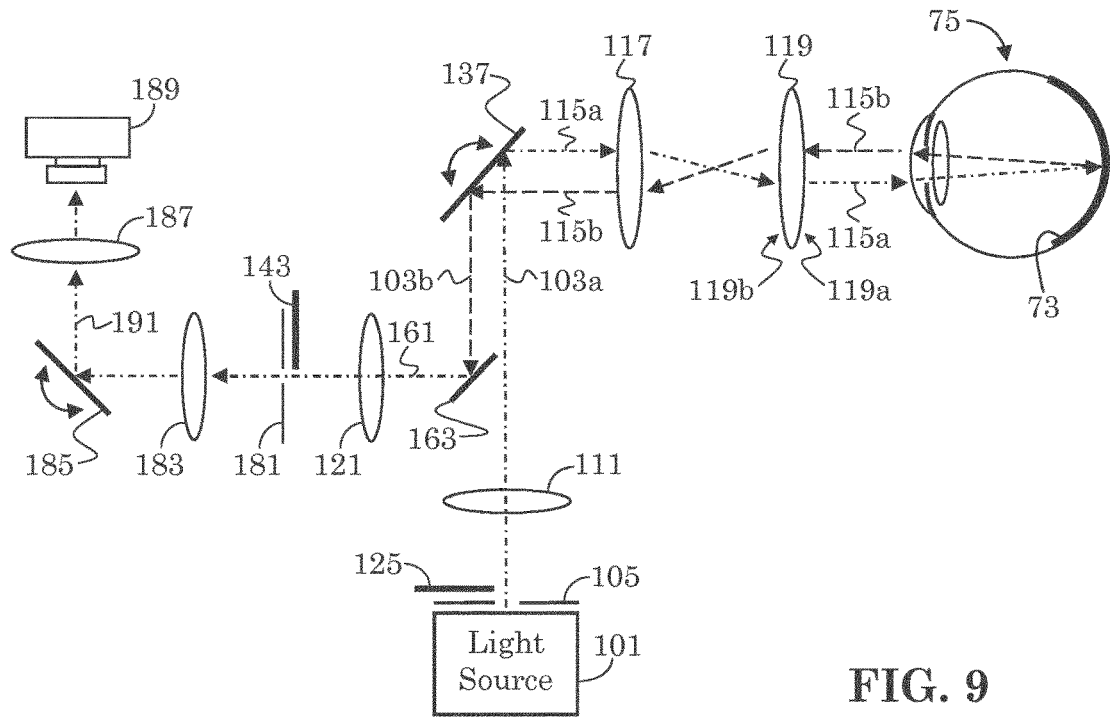
FIG. 9 illustrates an alternate scan-descan-rescan configuration example of a line scanning fundus imager incorporating the present invention.

FIG. 9 illustrates an alternate scan-descan-rescan configuration example of a slit (or line) fundus scan imager incorporating the present invention. Elements in FIG. 9 similar those of FIGS. 2 through 8 have similar reference characters and are discussed above. The scan-descan portion of the present configuration is similar to that of FIG. 7, but the present configuration differs from that of FIG. 7 by the incorporating a re-scan mechanism between its collector (e.g. camera 189) and collection block 143. That is, slit illumination from light source 101 follows illumination beam path (103a to 115a) through illumination slit 105, past a first beam block (e.g., illumination block) 125 through lens 111 to scanning component (e.g., galvo) 137, which creates a scan beam on optical path 115a. The scan beam on illumination path 115a passes through scan lens 117 and ophthalmic lens 119 and enters eye 75, where it is scanned incident on the retina 73. Light scattered from the retina 73 follows the collection beam path (115b to 103b to 161 to 191) back through ophthalmic lens 119 and scan lens 117, is descanned by rotating scan mirror 137, is deflected by pick-off mirror 163 onto optical path 161 to pass through lens 121 past a second beam block (e.g., collection block) 143 and passes through a collection slit (or aperture) 181, which may be located at a position corresponding to camera 131 of FIG. 7. Optionally, a collection (slit) aperture 181 may be at a conjugate plane of the retina 73. Returning light that passes collection aperture 181 passes through a (focusing) lens 183, and is rescanned by a second scanning component (second galvo) 185 that may be synchronized to scanning component 137. The rescanned returning light from second galvo 185 passes though optic 187 (which may be one or more lenses, such as a second scan lens and a focusing lens) to scan across camera 189, which may be a full-frame camera, to define a composite image.

In a scan-no-descan configuration (e.g., such as illustrated in FIG. 6A), where the illumination light is scanned, but the collected light is not descanned, one could still place an illumination block in the illumination path imaged to the ophthalmic lens (or other target optic) to reduce unwanted reflexes, but there may not be a practical corresponding place in the collection path to place such a collection block. Placement of a block only in the illumination path would reduce reflexes, but might not be as effective as placing blocks in both the illumination and collection paths to ensure no overlap between the illumination and collection paths at the ophthalmic lens.

The variation in refractive error of the eye across the human population may also complicate matters. To effectively image patients with different refractions (levels of myopia or hyperopia), fundus imagers typically have a focus adjustment to bring the image of the retina into focus on the camera sensor (e.g., the collector or detector). If this focus adjustment changes the location of the image (conjugate) plane of the ophthalmic lens (or other target optic) where the illumination and/or collection blocks are placed, it may be desirable to have the block locations move with the focus adjustment, so as to remain at the ophthalmic lens image plane. Alternatively, as the reflex issue is worse for more myopic patients, the blocks could be placed (e.g., fixed) at a position corresponding to the ophthalmic lens image plane for a relatively myopic patient (e.g., −10 diopters).

An alternate approach to maintaining the position of the illumination/collection blocks substantially constant relative to the image plane of the ophthalmic lens, is to keep the optics between the illumination/collection blocks and the ophthalmic lens fixed, and correct the focus to the camera between the illumination/collection blocks and the illumination source/camera, respectively. For example in the embodiment of FIG. 9, the position of collection block 143 may be maintained fixed at a conjugate plane of ophthalmic lens 119, while one or more lenses between camera 189 and collection block 143 (e.g., lens 183 and/or lens 187) is adjusted to bring the image of the retina 73 into focus on the photosensor of camera 189. It has been found that maintaining the focus of the illumination beam (e.g., on optical path 103a in FIG. 9) may not be as critical, so the illumination focus could either also be adjusted between the illumination block (e.g., 125) and the illumination source (e.g. 101/105), or the illumination block 125 may be left static as the camera focus is adjusted.

Although there is an optimum position for the illumination block and the collection block (e.g., at a conjugate plane of the target optic), some flexibility in their position has been identified. Providing a dead zone (e.g., 169 in FIG. 8), or overlap, between the imaged blocking regions (e.g., 125' and 143') may reduce the sensitivity to positioning of the illumination block and the collection block relative to the image plane corresponding to the ophthalmic lens (or other target optic). This overlap, or dead zone, may also be desirable for eliminating overlap between illumination and collection at the ophthalmic lens in the presence of optical aberrations in the system. Since a line scanning system (e.g., broad-line scanning imager) has a low etendue in the splitting direction (e.g. direction perpendicular to the length direction of the slit), a relatively small amount of overlap can lead to significant flexibility in the placement of the illumination block and the collection block.

It has further been found that for highly myopic patients (e.g., −6 diopter), the cornea may cause the retinal plane to be imaged to a plane close to the ophthalmic lens. Therefore, for highly myopic patients, blocking the overlap between illumination and collection paths at the ophthalmic lens may impact the overlap between illumination and collection at the retina, leading to a possible reduction in optical efficiency, and lower image brightness. It may therefore be desirable to have imaging modes for some myopic patients (e.g., highly myopic patients) where the illumination block and the collection block are removed, or pulled back a bit, to allow some overlap between illumination path and collection path at the ophthalmic lens, accepting some reflexes in the image in order to maintain an acceptable overall brightness and quality of the image.

While splitting the illumination and collection paths with a mirror 163 just before the scanning component 137, e.g., as shown in FIGS. 7 and 9, provides a relatively flexible design, it may create additional alignment steps as the deflection angle of the mirror becomes a free parameter. Conceptually, one could replace the mirror 163 with a wedge (e.g., see FIG. 6B) to deflect the collection path by a fixed angle, eliminating this free parameter. An issue with inserting a wedged optic or prism into the system is that reflections from the front and back surfaces of the wedge may create artifacts in the image. However, if the focusing optic is modified, adding a wedge to one side of it, may result in what is herein termed a "dual lens." Combining the dual lens into a single composite structure is herein termed a "composite dual lens."

FIG. 10 illustrates a conceptual design of a composite dual lens 209. As shown, it is desired to combine a lens 201 with a wedge 203. This may be achieved by combining the lens 201 with a prism 205 resulting in a conceptual dual lens 207, which may be constructed, e.g., molded, as a single component, resulting in a composite dual lens 209 that has a fixed spacing between two centroids C1 and C2.

Figure 11:
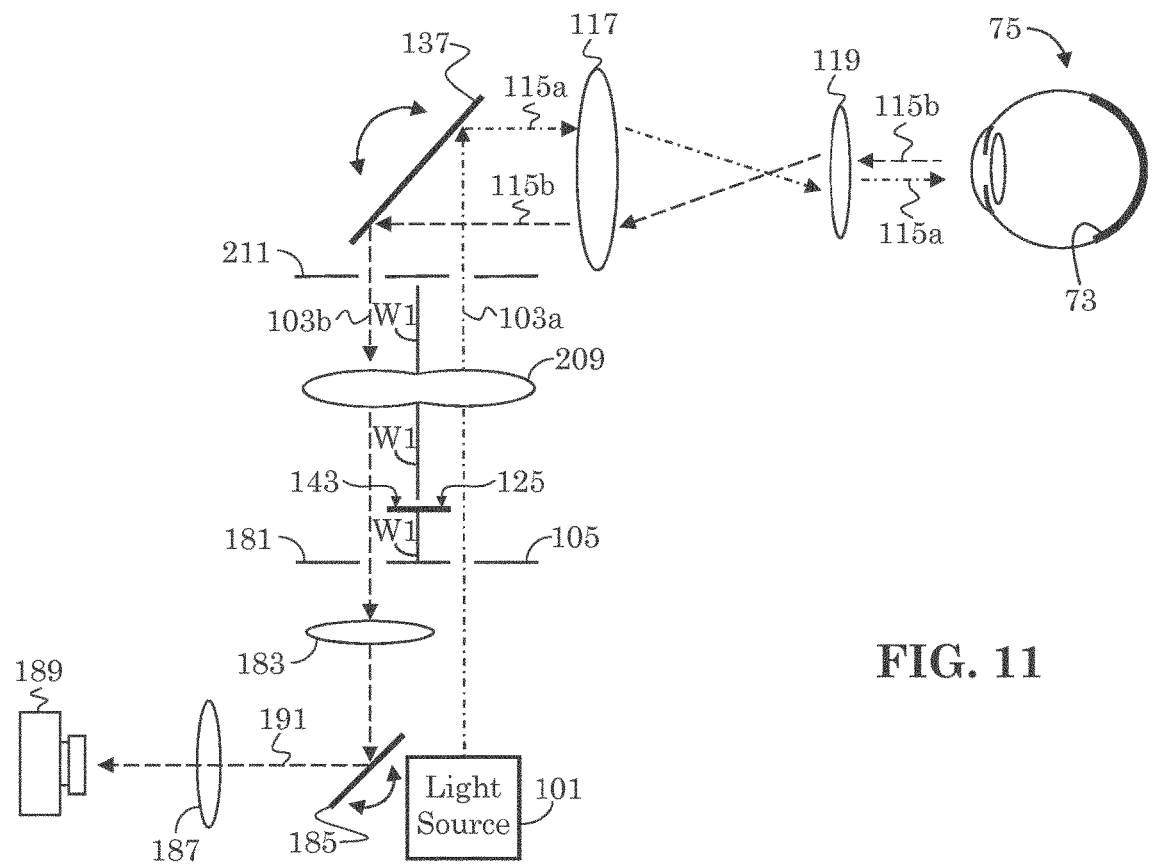
FIG. 11 illustrates an alternate structure for adding beam blocks imaged to an ophthalmic/ocular lens in a scan-descan-rescan line scanning system using a composite dual lens.

FIG. 11 illustrates an alternate structure for adding beam blocks (125/143) imaged to ophthalmic/ocular lens 119 in a scan-descan-rescan line scanning system using a composite dual lens 209. The use of composite dual lens 209 for separation of illumination and collection light paths may reduce both alignment steps and component count. All elements in FIG. 11 similar to those of FIGS. 2 through 10 have similar reference characters and are described above. In the present example, a pupil-splitting aperture 211 (or splitting region) may be positioned immediately preceding the scanning component 137 (e.g., in a path between light source 101 and scanning component 137), and imaged close to the cornea, e.g., assuming that scanning component 137 is imaged to the pupil, as described above. Additionally, ophthalmic lens 119 may be adjusted for myopia, and illumination block 125 and collection block 143 may be at a conjugate plane of ophthalmic lens 119 (e.g., corresponding to a myopic eye setting) for blocking reflexes. Also, radiation slit (aperture) 105 and collection slit (or aperture) 181 may be imaged to the retina 73, and further constructed on a common (the same) film, eliminating a need to align one to the other (e.g., displacement is determined by separation between dual lens) 209. Additionally, beam blocks 125/143 and slits 105/181 may move together, e.g., by virtue of a common (the same) supporting wall W1, and thereby maintain alignment. Supporting wall W1 may further provide a light barrier to separate illumination light on the side of light source 101 from collection light on a side of second scanning component 185 and collector 189.

In the present example, the illumination block 125 and collection block 143 may substantially be at the image plane of the ophthalmic (ocular) lens 119, be substantially coplanar, and may be manufactured from a single foil, providing high alignment accuracy between them. Likewise, the illumination slit 105 and collection slit 181 may also be coplanar and thus may be manufactured from a single foil. The alignment tolerance between the beam blocks 125/143 and the slits 105/181 may also be less strict than the relative alignment between the slits or between the beam blocks, and therefore this alignment may rely on accurate mounting between these two components, without a need for further alignment adjustment. The spacing between the two centroids C1 and C2 (see FIG. 10) of the composite dual lens 209 may be critical to the alignment, and thus it may be desirable to mold composite dual lens 209 as a single component.

In the descriptions above, the beam blocks (e.g., 143/125) have been imaged to the ophthalmic lens, as this lens may be an important component that creates reflexes in an ophthalmic scan imager. However, a similar approach of placing light blockers (e.g., additional or the same beam blocks) at the conjugate plane to a given target optic other than the ophthalmic lens may be used for blocking reflexes from this other target optic in the system.

Figure 12:
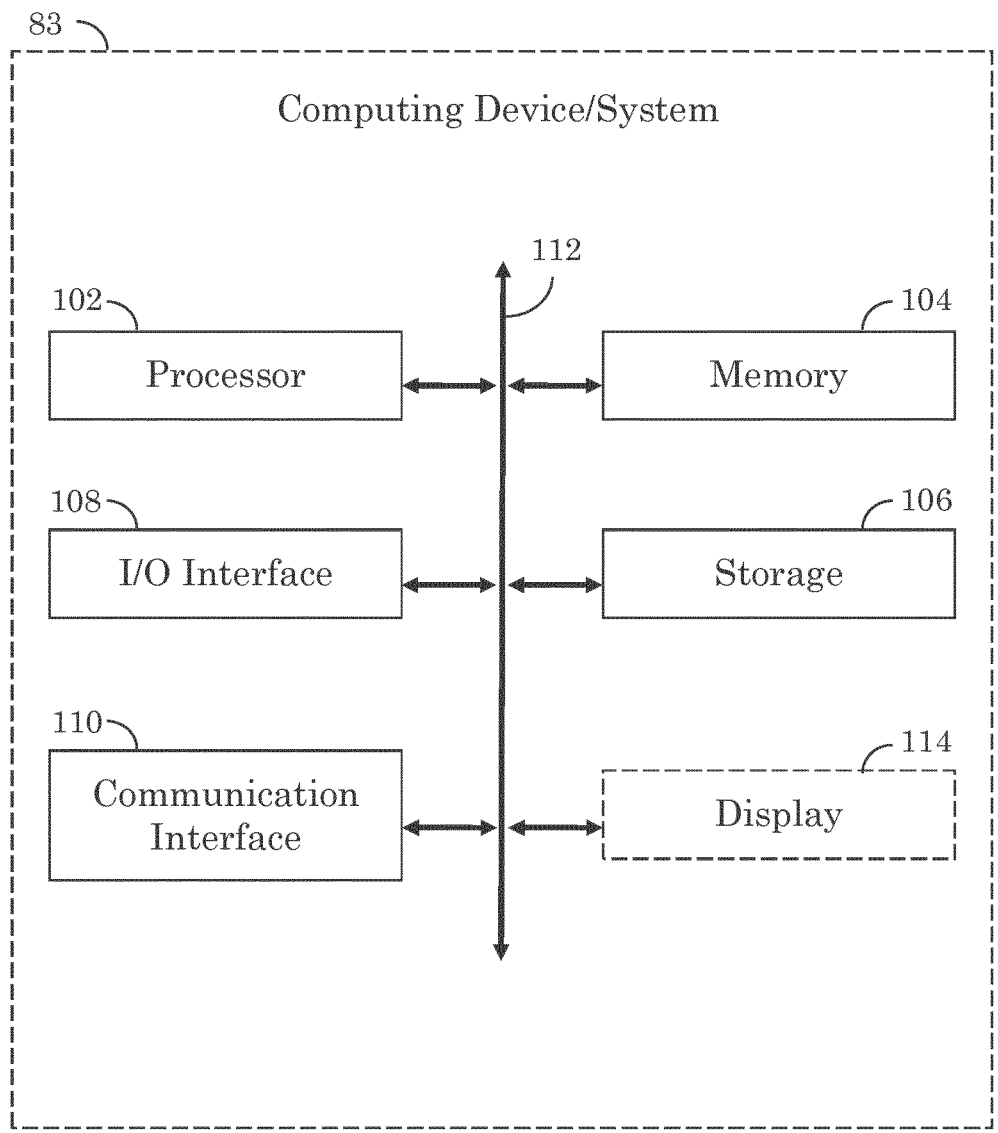
FIG. 12 illustrates an example computer device (or CPU or computer system).

FIG. 12 illustrates an example computer device (or CPU or computer system) 83. Computer device 83 may take any suitable physical form. For example, computer system 83 may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, or a combination of two or more of these. Where appropriate, computer device (or computer system) 83 may reside in a cloud, which may include one or more cloud components in one or more networks.

In some embodiments, computer system 83 includes one or more processor 102, memory 104, storage 106, an input/output (I/O) interface 108, a communication interface 110, and a bus 112. Computer system 83 may optionally also include a display 114, such as a computer monitor or screen (e.g., or display 85 as illustrated in FIG. 2). Processor 102 includes hardware for executing instructions, such as those making up a computer program. For example, processor 102 may be a central processing unit (CPU) or a general-purpose computing on graphics processing unit (GPGPU). Memory 104 may include main memory for storing instructions for processor 102 to execute or to hold interim data during processing. For example, memory 104 may include random access memory (RAM), such as dynamic RAM (DRAM) or static RAM (SRAM). In some embodiments, storage 106 may include long-term or mass storage for data or instructions. For example, storage 106 may include a hard disk drive (HDD or SSD), flash memory, ROM, EPROM, or other type of non-volatile memory. I/O interface 108 may include one or more interfaces for communication with I/O devices, which may enable communication with a person (user). Communication interface 110 may provide network interfaces for communication with other systems or networks. For example, communication interface 110 may include a network interface controller (NIC) and/or a wireless NIC for communication with another computer system on a network. Communication interface 110 may further include a Bluetooth interface or other type of packet-based communication. Bus 112 may provide a communication link between the above mentioned components of computing system 83.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications and variations as may fall within the spirit and scope of the appended claims.

The invention claimed is:

1. A scan imaging system comprising:
a radiation source;
a scanning component that receives radiation from the radiation source, and defines a scanning beam of radiation;
optics that direct the scanning beam of radiation to a sample to be imaged, the optics including a target optic element on which the scanning beam of radiation is scanned;
a radiation-blocking component positioned to partially block radiation output from the radiation source and to limit the radiation received by the scanning component, the radiation-blocking component being at a conjugate plane of the target optic element and creating a moving non-radiation zone on the target optic element through which the scanning beam of radiation may not pass, a portion of the scanning beam outside the moving non-radiation zone being scanned across the sample creating a moving region of illumination on the sample; and
a collector for collecting returning radiation from the moving region of illumination.

2. The scan imaging system of claim 1, wherein the radiation-blocking component is positioned along a radiation path from the radiation source to the scanning component.

3. The scan imaging system of claim 1, further comprising:
a collector-blocking component positioned to partially block radiation returning from the moving region of illumination, the collector-blocking component being at a conjugate plane of the target optic element and creating a moving non-collection zone on the target optic through which radiation returning from the moving region of illumination may not pass.

4. The scan imaging system of claim 3, wherein the moving non-radiation zone moves in conjunction with, and at least partially overlaps, the moving non-collection zone on the target optic.

5. The scan imaging system of claim 3, wherein the moving non-radiation zone moves in conjunction with, and abuts, the moving non-collection zone on the target optic.

6. The scan imaging system of claim 3, wherein:
the scan imaging system has a first operating mode in which the radiation-blocking component is positioned to partially block radiation output from the radiation source and the collector-blocking component is positioned to partially block radiation returning from the moving region of illumination; and
the scan imaging system has a second operating mode in which the radiation-blocking component is positioned to not obstruct radiation output from the radiation source and the collector-blocking component is positioned to not obstruct radiation returning from the moving region of illumination.

7. The scan imaging system of claim 6 wherein:
the sample to be imaged is an eye;
the first operating mode corresponds to non-myopic eyes; and
the second operating mode correspond to myopic eyes of greater than a predefined diopter value.

8. The scan imaging system of claim 3, further comprising:
a focus-adjustment mechanism that brings the sample into focus on the collector; wherein:
focusing the sample onto the collector causes the conjugate plane of the target optic element to move; and
the collector-blocking component moves in conjunction with the conjugate plane of the target optic element to remain on the conjugate plane of the target optic element.

9. The scan imaging system of claim 8, wherein:
the position of the radiation-blocking component remains static irrespective of movement of the conjugate plane of the target optic element due to focusing of the sample onto the collector.

10. The scan imaging system of claim 3, further comprising:
focus-adjusting optics that bring the sample into focus on the collector, the focus-adjusting optics being between the collector-blocking component and the collector; wherein:
the relative positions all optics along a radiation returning path from the target optic element to the collector-blocking component are fixed; and
the collector-blocking component remains static and at the conjugate plane of the target optic element while the focus-adjusting optics focus the sample onto the collector.

11. The scan imaging system of claim 3, wherein the radiation-blocking component is coplanar with the collector-blocking component.

12. The scan imaging system of claim 11, further comprising:
an illumination aperture on a conjugate plane of a surface of the sample to be imaged, the illumination aperture being between the illumination source and the radiation-blocking component;
a collection aperture at a conjugate plane of the surface of the sample to be imaged, the collection aperture being between the collector and the collector-blocking component;
wherein the illumination aperture is coplanar with the collection aperture.

13. The scan imaging system of claim 12, further comprising:
a splitting region substantially imaged to a position immediately preceding the scanning component in a radiation path from the radiation source to the scanning component, the splitting region separating the scanning beam of radiation at the sample from radiation returning from the sample, the splitting region having a first sample-opening through which the scanning beam of radiation passes and a second sample-opening through which radiation returning from the sample passes, the first sample-opening and second sample-opening being coplanar;

a dual lens embodied by two coplanar lenses molded as a single optic component, the dual lens including a first sub-lens aligned with the first sample-opening and a second sub-lens aligned to the second sample-opening;

a structural support maintaining alignment between the first sample-opening, the first sub-lens, the radiation-blocking component, and the illumination aperture, and maintaining alignment between the second sample-opening, the second sub-lens, the collector-blocking component, and the collector aperture.

14. The scan imaging system of claim 1, wherein:

the sample to be imaged is an eye having a pupil and a fundus;

the scanning beam of radiation enters the eye through the pupil and creates the moving region of illumination on the fundus; and radiation returning from the moving region of illumination exits the eye through the pupil;

the system further comprising:

radiation apertures positioned in front of the radiation source, the radiation apertures being imaged substantially to the fundus;

pupil splitting optics imaged substantially to the pupil of the eye, the pupil splitting optics separating the scanning beam of radiation entering the eye from the returning radiation exiting the eye, the pupil splitting optics including a pupil-aperture imaged substantially to the pupil;

wherein the radiation-blocking component is positioned between the pupil-aperture and the radiation aperture.

15. The scan imaging system of claim 1, wherein the target optic element is a system lens positioned in a radiation path from the scanning component to the sample to be imaged.

16. The scan imaging system of claim 15, wherein the system lens is closest to the sample on the radiation path from the scanning component to the sample.

17. The scan imaging system of claim 1, wherein the radiation source is one of a laser source and an incoherent radiation source.

18. The scan imaging system of claim 1, wherein the radiation output from the radiation source is a substantially rectangular beam of radiation.

19. The scan imaging system of claim 18, wherein the rectangular beam of radiation has a length dimension and a variable width dimension substantially perpendicular to the length dimension.

20. The scan imaging system of claim 1, wherein the scan imaging system is one of a point-scanning imager and a line scanning imager.

21. The scan imaging system of claim 1, wherein the scan imaging system is one of a scan-no-descan system, a scan-descan system, and a scan-descan-rescan system.

22. The scan imaging system of claim 1, further including a spherical mirror to counter field curvature aberrations of one or more lenses of the scan imaging system.

23. The scan imaging system of claim 22, wherein the radius of curvature of the spherical mirror is adjusted along the plane of reflection of the incident beam to reduce or eliminate an astigmatism of the spherical mirror.

24. The scan imaging system of claim 1, further including:

a first spherical mirror; and a second spherical mirror positioned to receive a reflected signal from the first spherical mirror and having a plane of reflection orthogonal to a plane of reflection at the first spherical mirror to counter an astigmatism of the first spherical mirror.

25. The scan imaging system of claim 1, further comprising cross polarizers, including a first polarizer positioned in the optical path from the radiation source to the sample, and a second polarizer in an orthogonal state relative to the first polarizer and positioned in the optical path from the sample to the collector.

* * * * *